US010449176B2

(12) United States Patent
Dressman et al.

(10) Patent No.: US 10,449,176 B2
(45) Date of Patent: *Oct. 22, 2019

(54) TREATMENT OF CIRCADIAN RHYTHM DISORDERS

(71) Applicant: Vanda Pharmaceuticals Inc., Washington, DC (US)

(72) Inventors: Marlene Michelle Dressman, Germantown, MD (US); Louis William Licamele, Potomac, MD (US); Mihael H. Polymeropoulos, Potomac, MD (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,162

(22) Filed: Nov. 26, 2017

(65) Prior Publication Data

US 2018/0071245 A1 Mar. 15, 2018

Related U.S. Application Data

(60) Continuation of application No. 15/378,353, filed on Dec. 14, 2016, now Pat. No. 9,855,241, which is a division of application No. 14/374,257, filed as application No. PCT/US2013/023315 on Jan. 25, 2013, now Pat. No. 9,549,913.

(60) Provisional application No. 61/755,896, filed on Jan. 23, 2013, provisional application No. 61/738,987, filed on Dec. 18, 2012, provisional application No. 61/738,985, filed on Dec. 18, 2012, provisional application No. 61/714,149, filed on Oct. 15, 2012, provisional application No. 61/650,455, filed on May 22, 2012, provisional application No. 61/650,458, filed on May 22, 2012, provisional application No. 61/640,067, filed on Apr. 30, 2012, provisional application No. 61/590,974, filed on Jan. 26, 2012.

(51) Int. Cl.
*A61K 31/343* (2006.01)
*A61K 31/00* (2006.01)
*G01N 33/68* (2006.01)
*A61K 9/00* (2006.01)
*A61K 45/06* (2006.01)
*A61K 31/15* (2006.01)
*A61K 31/277* (2006.01)
*A61K 31/496* (2006.01)

(52) U.S. Cl.
CPC ............ *A61K 31/343* (2013.01); *A61K 9/006* (2013.01); *A61K 9/0053* (2013.01); *A61K 31/00* (2013.01); *A61K 31/15* (2013.01); *A61K 31/277* (2013.01); *A61K 31/496* (2013.01); *A61K 45/06* (2013.01); *G01N 33/6893* (2013.01); *G01N 2800/2864* (2013.01)

(58) Field of Classification Search
CPC .............................. A61K 31/343; A61K 9/00
See application file for complete search history.

(56) References Cited

U.S. PATENT DOCUMENTS

| 4,880,826 | A | 11/1989 | Zisapel et al. |
| 4,997,845 | A | 3/1991 | Flaugh |
| 5,093,352 | A | 3/1992 | Dubocovich |
| 5,151,446 | A | 9/1992 | Horn et al. |
| 5,225,442 | A | 7/1993 | Andrieux et al. |
| 5,430,029 | A | 7/1995 | Biella et al. |
| 5,580,878 | A | 12/1996 | D'Orlando et al. |
| 5,840,341 | A | 11/1998 | Watts et al. |
| 5,856,529 | A | 1/1999 | Cat et al. |
| 6,180,657 | B1 | 1/2001 | Flaugh |
| 6,211,225 | B1 | 4/2001 | Takaki et al. |
| 6,348,485 | B1 | 2/2002 | Ohkawa et al. |
| 6,403,651 | B1 | 6/2002 | Kennaway |
| 7,754,902 | B2 | 7/2010 | Pereira et al. |
| 8,785,492 | B2 | 7/2014 | Dressman et al. |
| 9,539,234 | B2 | 1/2017 | Dressman et al. |
| 9,549,913 | B2 | 1/2017 | Dressman et al. |
| 9,730,910 | B2 | 8/2017 | Dressman et al. |
| 9,855,241 | B2 * | 1/2018 | Dressman ............ A61K 31/343 |
| 2001/0047016 | A1 | 11/2001 | Oxenkrug |
| 2005/0137247 | A1 | 6/2005 | Czeisler et al. |
| 2005/0164987 | A1 | 7/2005 | Barberich |
| 2007/0270593 | A1 | 11/2007 | Pereira et al. |
| 2009/0105333 | A1 | 4/2009 | Birznieks et al. |
| 2010/0261786 | A1 | 10/2010 | Lavedan et al. |

FOREIGN PATENT DOCUMENTS

| CA | 2652421 A1 | 11/2007 |
| CA | 2666293 C | 11/2007 |
| FR | 2329275 A1 | 5/1977 |
| JP | H05155769 A | 6/1993 |
| JP | H10-513177 A | 12/1998 |

(Continued)

OTHER PUBLICATIONS

Klerman et al., "Analysis method and experimental conditions affect computed circadian phase from melatonin data", (2012) PLoS. ONE. 7, e33836.

(Continued)

*Primary Examiner* — Golam M Shameem

(74) *Attorney, Agent, or Firm* — Hoffman Warnick LLC

(57) ABSTRACT

Embodiments of the invention relate to the use of a melatonin agonist in the treatment of free running circadian rhythms in patients, including light perception impaired patients, e.g., blind patients, and to methods of measuring circadian rhythm.

9 Claims, 11 Drawing Sheets

(56) References Cited

FOREIGN PATENT DOCUMENTS

| | | |
|---|---|---|
| JP | H1151014 A | 12/1999 |
| JP | 2005-080603 A | 3/2005 |
| JP | 2006525317 A | 11/2006 |
| JP | 2010215561 A | 9/2010 |
| WO | 03037337 A1 | 5/2003 |
| WO | 2004006886 A2 | 1/2004 |
| WO | 2005063297 A2 | 7/2005 |
| WO | 2007016203 A1 | 2/2007 |
| WO | 2007137244 A1 | 11/2007 |
| WO | 2009036257 A1 | 3/2009 |
| WO | 2009058261 A1 | 5/2009 |
| WO | 2009084023 A2 | 7/2009 |
| WO | 2011009102 A1 | 1/2011 |
| WO | 2013112949 | 8/2013 |
| WO | 2014100292 | 6/2014 |

OTHER PUBLICATIONS

Klerman et al., "Nonphotic entrainment of the human circadian pacemaker", (1998) Am.J.Physiol 274,R991-R996.
Lancel et al., "Effect of the GABAA agonist gaboxadol on nocturnal sleep and hormone secretion in healthy elderly subjects", (2001) Am J Physiol Endocrinol Metab. 1, E130-137.
Leger et al., "Prevalence of sleep/wake disorders in persons with blindness", (1999) Clin Sci (Lond) 97,193-199.
Leger et al., "Sleep/wake cycles in the dark: sleep recorded by polysomnography in 26 totally blind subjects compared to controls", (2002) Clin Neurophysiol. 113,1607-1614.
Lewy, A. J. "Melatonin as a marker and phase-resetter of circadian rhythms in humans", (1999) Adv. Exp. Med. Biol. 460, 425-434.
Lewy, A. J. "Melatonin and human chronobiology", (2007) Cold Spring Harb. Symp. Quant. Biol. 72, 623-636.
Lewy et al., "The human phase response curve (PRC) to melatonin is about 12 hours out of phase with the PRC to light", (1998) Chronobiol. Int. 15, 71-83.
Lewy et al., "Capturing the circadian rhythms of free-running blind people with 0.5 mg melatonin", (2001) Brain Res. 918, 96-100.
Lewy et al., "Eventual Entrainment of the human circadian pacemaker by melatonin is independent of the circadian phase of treatment initiation: clinical implications", (2004) J Biol Rhythms 19, 68-75.
Lewy et al, "Circadian uses of melatonin in humans", (2006) Chronobiol. Int. 23, 403-412.
Lewy et al., "The endogenous melatonin profile as a marker for circadian phase position", (1999) J.Biol.Rhythms 14, 227-236.
Lewy et al., "Low, but not high, doses of melatonin entrained a free-running blind person with a long circadian period", (2002) Chronobiol.Int. 19, 649-658.
Lewy, A.J., "Current understanding and future implications of the circadian uses of melatonin, a neurohormone discovered by Aaron B. Lerner", (2007) J Invest Dermatol. 127, 2082-2085.
Lockley et al., "Alertness, mood and performance rhythm disturbances associated with circadian sleep disorders in the blind", (2008) J Sleep Res. 17, 207-216.
Lockley et al., "Melatonin administration can entrain the free-running circadian system of blind subjects", (2000) J. Endocrinol. 164, R1-R6.
Lockley et al., "Visual impairment and circadian rhythm disorders.", (2007) Dialogues Clin Neurosci. 9, 301-314.
Lockley et al., "Comparison between subjective and actigraphic measurement of sleep and sleep rhythms", (1999) J Sleep Res. 8, 175-783.
Lucas et al., "Free running circadian rhythms of melatonin, luteinizing hormone, and cortisol in Syrian hamsters bearing the circadian tau mutation", (1999) Endocrinology 140, 758-764.
Mikulich et al., "Comparing linear and nonlinear mixed model approaches to cosinor analysis", (2003) Stat. Med. 22, 3195-3211.
Miles et al., "Blind man living in normal society has circadian rhythms of 24.9 hours", (1977) Science 198, 421-423.
Morgan et al., "Effects of the endogenous clock and sleep time on melatonin, insulin, glucose and lipid metabolism", (1998) J Endocrinol 157, 443-451.
Morgenthaler et al., "Practice parameters for the clinical evaluation and treatment of circadian rhythm sleep disorders. An American Academy of Sleep Medicine report", (2007) Sleep 30,1445-1459.
Mundey et al., "Phase-dependent treatment of delayed sleep phase syndrome with melatonin", (2005) Sleep 28, 1271-1278.
Nakagawa et al., "Sleep propensity free-runs with the temperature, melatonin and cortisol rhythms in a totally blind person", (1992) Sleep 15, 330-336.
Nathan et al., "The effect of atenolol, a beta1-adrenergic antagonist, on nocturnal plasma melatonin secretion: evidence for a dose-response relationship in humans", (1997) J Pineal Res 23, 131-135.
Nickelsen et al., "Chronobiotic effects of the melatonin agonist LY 156735 following a simulated 9h time shift: results of a placebo-controlled trial", (2002) Chronobiol.Int. 19, 915-936.
Okamura, H. "Suprachiasmatic nucleus clock time in the mammalian circadian system", (2007) Cold Spring Harb. Symp. Quant. Biol 72, 551-556.
Okamura, H. "Integration of mammalian circadian clock signals: from molecule to behavior", (2003) J.Endocrinol. 177, 3-6.
Pandi-Perumal et al., "Dim light melatonin onset (DLMO): a tool for the analysis of circadian phase in human sleep and chronobiological disorders", (2007) Prog. Neuropsychopharmacol. Biol. Psychiatry 31, 1-11.
Pandi-Perumal et al, "Melatonin: Nature's most versatile biological signal?", (2006) FEBS J 273, 2813-2838.
Pandi-Perumal et al., "The effect of melatonergic and non-melatonergic antidepressants on sleep: weighing the alternatives", (2008) World J Biol Psychiatry 10, 342-354.
Pandi-Perumal et al., "Physiological effects of melatonin: role of melatonin receptors and signal transduction pathways", (2008) Prog.Neurobiol. 85, 335-353.
Paulis et al., "Cardiovascular effects of melatonin receptor agonists", (2012) Expert.Opin.Investig.Drugs 21,1661-1678.
Rajaratnam et al., "Melatonin phase-shifts human circadian rhythms with no evidence of changes in the duration of endogenous melatonin secretion or the 24-hour production of reproductive hormones", (2003) J Clin Endocrinol. Metab 88, 4303-4309.
Revell et al., "Circadian phase determined from melatonin profiles is reproducible after 1 wk in subjects who sleep later on weekends", (2005) J. Pineal Res. 39, 195-200.
Revell et al., "Advancing human circadian rhythms with afternoon melatonin and morning intermittent bright light", (2006) J Clin Endocrinol Metab 91, 54-59.
Richardson et al., "Circadian phase-shifting effects of repeated ramelteon administration in healthy adults", (2008) J. Clin.Sleep Med. 4, 456-461.
Sack et al., "Circadian rhythm sleep disorders: lessons from the blind", (2001) Sleep Med Rev. 5, 189-206.
Sack et al., "Circadian rhythm abnormalities in totally blind people: incidence and clinical significance", (1992) J. Clin. Endocrinol. Metab 75, 127-134.
Sack et al., "Circadian rhythm sleep disorders: part II, advanced sleep phase disorder, delayed sleep phase disorder, free-running disorder, and irregular sleep-wake rhythm", (2007) Sleep 30,1484-1501.
Scheer et al., "Plasticity of the intrinsic period of the human circadian timing system", (2007) PLoS. ONE. 2, e721.
Scheer et al., "Adverse metabolic and cardiovascular consequences of circadian misalignment", (2009) Proc.Natl. Acad.Sci U.S.A 106, 4453-4458.
Shanahan et al., "Melatonin rhythm observed throughout a three-cycle bright-light stimulus designed to reset the human circadian pacemaker", (1999) J. Biol. Rhythms 14, 237-253.
Shanahan et al., "Resetting the melatonin rhythm with light in humans", (1997) J. Biol. Rhythms 12, 556-567.
Skene et al., "Melatonin in circadian sleep disorders in the blind", (1999) Biol. Signals Recept. 8, 90-95.
Skene et al., "Circadian rhythm sleep disorders in the blind and their treatment with melatonin", (2007) Sleep Med. 8, 651-655.

(56) References Cited

OTHER PUBLICATIONS

Skene et al., "Correlation between urinary cortisol and 6-sulphatoxymelatonin rhythms in field studies of blind subjects", (1999) Clin Endocrinol (Oxf) 50, 715-719.
Srinivasan et al., "Jet lag, circadian rhythm sleep disturbances, and depression: the role of melatonin and its analogs", (2010)Adv.Ther. 27, 796-813.
St Hilaire et al., "Human Phase Response Curve (PRC) to a 1-hour Pulse of Bright White Light", (2012) J. Physiol.
Hetiloz, "Accessibility Policy," retrieved from: http://www.hetiloz.com/accessibility-policy.php, Oct. 16, 2013, 3 pages.
Srinivassan et al., "Progress in Neuro-Psychopharmacology & Biological Psychiatry," 35, 2011, pp. 913-923.
Cain et al., "Exercise distributed across day and night does not alter circadian period in humans", (2007) J. Biol. Rhythms 22, 534-541.
Czeisler et al., "Human sleep: its duration and organization depend on its circadian phase", (1980) Science 210,1264-1267.
Dubocovich,M.L. "Melatonin receptors: role on sleep and circadian rhythm regulation", (2007) Sleep Med. Suppl 3: 34-42.
Lewy et al., "Zeitgeber hierarchy in humans: resetting the circadian phase positions of blind people using melatonin", (2003) Chronobiol. Int. 20, 837-852.
Lewy et al., "Melatonin entrains free-running blind people according to a physiological dose-response curve", (2005) Chronobiol.Int. 22,1093-1106.
Lockley et al., "Day-time naps and melatonin in blind people", (1995) Lancet 346,1491.
Scheer et al., "Melatonin, sleep, and circadian rhythms", (2005) Sleep Med Rev. 9, 5-9.
Van Den Heuvel et al., "Effect of atenolol on nocturnal sleep and temperature in young men: reversal by pharmacological doses of melatonin", (1997) Physiol Behav 61, 795-802.
Cameron et al., "Effect of Atenolol on Nocturnal Sleep and Temperature in Young Men: Reversal by Pharmacological Doses of Melatonin," 1997, pp. 795-802, Physiology & Behavior, vol. 61, No. 6.
Rajaratnam et al., "Melatonin agonist tasimelteon (VEC-162) for transient insomnia after sleep-time shift: two randomised controlled multicentre trials," 2008, pp. 1-10, published online at www.thelancet.com.
Rajaratnam et al., Webappendix, "Melatonin agonist tasimelteon (VEC-162) for transient insomnia after sleep-time shift: two randomised controlled multicentre trials," 2008, pp. 1-2, published online at www.thelancet.com.
Archer et al., "Inter-individual differences in habitual sleep timing and entrained phase of endogenous circadian rhythms of BMAL1, PER2 and PER3 mRNA in human leukocytes", (2008) Sleep 31,608-617.
Arendt, J. "Importance and relevance of melatonin to human biological rhythms", Arendt, J. (2003) J. Neuroendocrinol. 15, 427-431.
Arendt et al. "Immunoassay of 6-hydroxymelatonin sulfate in human plasma and urine: abolition of the urinary 24-hour rhythm with atenolol", (1985) J. Clin. Endocrinol. Metab 60, 1166-1173.
Arendt et al. "Efficacy of melatonin treatment in jet lag, shift work, and blindness", (1997) J. Biol. Rhythms 12, 604-617.
Arendt, J. "Melatonin and the pineal gland: influence on mammalian seasonal and circadian physiology", (1998) Rev. Reprod. 3, 13-22.
Arendt et al., Melatonin and its agonists: an update:, (2008) Br.J Psychiatry 193, 267-269.
Boivin et al., "Complex interaction of the sleep-wake cycle and circadian phase modulates mood in healthy subjects", (1997) Arch. Gen. Psychiatry 54, 145-152.
Bojkowski et al., "Melatonin secretion in humans assessed by measuring its metabolite, 6-sulfatoxymelatonin", (1987) Clin. Chem. 33, 1343-1348.
Buijs et al., "The biological clock tunes the organs of the body: timing by hormones and the autonomic nervous system", (2003) J.Endocrinol. 177,17-26.

Burgess et al., "Individual differences in the amount and timing of salivary melatonin secretion", (2008) PLoS.ONE.3, e3055.
Burgess et al., "Human phase response curves to three days of daily melatonin: 0.5 mg versus 3.0 mg", (2010) J. Clin. Endocrinol. Metab 95, 3325-3331.
Burgess et al., "A three pulse phase response curve to three milligrams of melatonin in humans", (2008) J Physiol 586,639-647.
Cain et al., "Sex differences in phase angle of entrainment and melatonin amplitude in humans", (2010) J Biol Rhythms 25, 288-296.
Campbell et al., "Etiology and treatment of intrinsic circadian rhythm sleep disorders", (1999) Sleep Med Rev. 3,179-200.
Carskadon et al., "Intrinsic circadian period of adolescent humans measured in conditions of forced desynchrony", (1999) Neurosci. Lett. 260, 129-132.
Chang et al., "The human circadian system adapts to prior photic history", (2011) J. Physiol 589, 1095-1102.
Cohen et al, "Ramelteon prior to a short evening nap impairs neurobehavioral performance for up to 12 hours after awakening", (2010) J Clin Sleep Med. 5, 565-571.
Cowen et al., "Treatment with beta-adrenoceptor blockers reduces plasma melatonin concentration", (1985) Br J Clin Pharmacol 19, 258-260.
Cowen et al., "Atenolol reduces plasma melatonin concentration in man", (1983) Br J Clin Pharmacol 15, 579-581.
Czeisler et al., "Sleep and circadian rhythms in humans", (2007) Cold Spring Harb. Symp. Quant. Biol. 72, 579-597.
Czeisler et al., "Bright light induction of strong (type 0) resetting of the human circadian pacemaker", (1989) Science 244, 1328-1333.
Czeisler et al., "Bright light resets the human circadian pacemaker independent of the timing of the sleep-wake cycle", (1986) Science 233, 667-671.
Czeisler et al., "Suppression of melatonin secretion in some blind patients by exposure to bright light", (1995) N.Engl.J. Med 332, 6-11.
Czeisler et al., "Stability, precision, and near-24-hour period of the human circadian pacemaker", (1999) Science 284, 2177-2181.
Czeisler et al., "Circadian and sleep-dependent regulation of hormone release in humans", (1999) Recent Prog.Horm. Res 54, 97-130.
Dijk et al., "Amplitude reduction and phase shifts of melatonin, cortisol and other circadian rhythms after a gradual advance of sleep and light exposure in humans", (2012) PLoS. ONE. 7, e30037.
Dijk et al., "Variation of electroencephalographic activity during non-rapid eye movement and rapid eye movement sleep with phase of circadian melatonin rhythm in humans", (1997) J. Physiol 505 ( Pt 3), 851-858.
Dijk et al., "Contribution of the circadian pacemaker and the sleep homeostat to sleep propensity, sleep structure, electroencephalographic slow waves, and sleep spindle activity in humans", (1995) J Neurosci 15, 3526-3538.
Dubocovich et al., "Molecular pharmacology, regulation and function of mammalian melatonin receptors", (2003) Front Biosci. 8, d1093-d1108.
Dubocovich,M.L, "Melatonin receptors: are there multiple subtypes? ", (1995) Trends Pharmacol.Sci. 16, 50-56.
Dubocovich et al., "Selective MT2 melatonin receptor antagonists block melatonin-mediated phase advances of circadian rhythms", (1998) FASEB J 12, 1211-1220.
Dubocovich et al., "Functional MT1 and MT2 melatonin receptors in mammals", (2005) Endocrine 27,101-110.
Duffy et al., "Entrainment of the human circadian system by light", (2005) J Biol Rhythms 20, 326-38.
Duffy et al., "Quantification of Behavior Sackler Colloquium: Sex difference in the near-24-hour intrinsic period of the human circadian timing system", (2011) Proc. Natl. Acad. Sci. U. S. A 108 Suppl 3, 15602-15608.
Ekmekcioglu et al., "The melatonin receptor subtype MT2 is present in the human cardiovascular system", (2003) J. Pineal Res. 35, 40-44.
Emens et al., "Rest-activity cycle and melatonin rhythm in blind free-runners have similar periods", (2010) J. Biol. Rhythms 25, 381-384.

(56) References Cited

OTHER PUBLICATIONS

Emens et al., "Non-24-Hour Disorder in Blind Individuals Revisited: Variability and the Influence of Environmental Time Cues", (2013) Sleep 36,1091-1100.
Fischer et al., "Melatonin acutely improves the neuroendocrine architecture of sleep in blind individuals", (2003) J Clin Endocrinol Metab 88, 5315-5320.
Gonnissen et al., "Effect of a phase advance and phase delay of the 24-h cycle on energy metabolism, appetite, and related hormones", (2012) Am.J.Clin.Nutr. 96, 689-697.
Gooley et al., "Exposure to Room Light before Bedtime Suppresses Melatonin Onset and Shortens Melatonin Duration in Humans", (2011) J Clin Endocrinol Metab 96, E463-E472.
Gooley et al., "Spectral responses of the human circadian system depend on the irradiance and duration of exposure to light", (2010) Sci. Transl. Med. 2, 31ra33.
Gronfier et al., "Entrainment of the human circadian pacemaker to longer-than-24-h days", (2007) Proc. Natl. Acad. Sci U. S. A 104, 9081-9086.
Hack et al., "The effects of low-dose 0.5-mg melatonin on the free-running circadian rhythms of blind subjects", (2003) J. Biol. Rhythms 18, 420-429.
Hardeland,R., "Investigational melatonin receptor agonists", (2010) Expert.Opin.Investig.Drugs 19, 747-764.
Hardeland et al, "Melatonin and Synthetic Melatonergic Agonists: Actions and Metabolism in the Central Nervous System", (2012) Cent.Nerv.Syst.Agents Med.Chem. 12, 189-216.
Hasan et al., "Assessment of circadian rhythms in humans: comparison of real-time fibroblast reporter imaging with plasma melatonin", (2012) FASEB J.
Iwata et al., "Diurnal Cortisol Changes in Newborn Infants Suggesting Entrainment of Peripheral Circadian Clock in Utero and at Birth", (2012) J Clin Endocrinol Metab E25-32.
Kelly et al., "Nonentrained circadian rhythms of melatonin in submariners scheduled to an 18-hour day", (1999) J. Biol. Rhythms 14, 190-196.
Klein et al., "Circadian sleep regulation in the absence of light perception: chronic non-24-hour circadian rhythm sleep disorder in a blind man with a regular 24-hour sleep-wake schedule.", (1993) Sleep 16, 333-343.
Klerman et al., "Comparisons of the variability of three markers of the human circadian pacemaker", (2002) J. Biol. Rhythms 17, 181-193.
Ogilvie et al., "Clinical Assessment of Drug-Drug Interactions of Tasimelteon, a Novel Dual Melatonin Receptor Agonist," Drug Interactions, The Journal of Clinical Pharmacology, 2015, 55(9) 1004-1011.
Office Action for U.S. Appl. No. 14/301,918, dated May 11, 2015, 45 pages.
Office Action for U.S. Appl. No. 14/301,837, dated May 11, 2015, 46 pages.
Choy et al., " Jet Lag: Currect and Potential Therapies," P&T, 4(36): 221-231 (2011).
Van Harten, J., "Overview of the pharmacokinetics of fluvoxamine," Abstract, Clin Pharmacokinet., 1995; 29 Suppl. 1:1-9.
Quera Salva et al., "Circadian Rhythms, Melatonin and Depression," Current Pharmaceutical Design, 2011, vol. 17, No. 15, pp. 1459-1470.
Office Action for Canadian Patent Application No. 2,861,108, dated Aug. 26, 2015, 5 pages.
Sack et al., "Entrainment of Free-Running Circadian Rhythms by Melatonin in Blind People," Dec. 2000, pp. 1070-1077, New England Journal of Medicine (XP055057908).
Okawa et al., "Circadian rhythm sleep disorders: Characteristics and entrainment pathology in delayed sleep phase and non-24 sleep-wake syndrome," 2007, pp. 485-496, Elsevier, Sleep Medicine (XP022341295).
Uchiyama et al., "Non-24-Hour Sleep-Wake Syndrome in Sighted and Blind Patients," 2009, pp. 195-211, Sleep Medicine Clinics, W.B. Saunders Co., Vo. 4, No. 2 (XP008161124).

Rajaratnam et al., "Melatonin agonist tasimelteon (VEC-162) for transient insomnia after sleep-time shift: two randomised controlled multicentre trials," 2009, pp. 482-491, The Lancet, vol. 373, No. 9662 (XP025913508).
Hardeland, "Tasimelteon, a melatonin agonist for the treatment of insomnia and circadian rhythm sleep disorders," 2009, pp. 691-701, Current Opinion in Investigational Drugs, Thomson Rueters (Scientific) Ltd., vol. 10, No. 7 (XP008161049).
Hardeland, "New approaches in the management of insomnia: Weighing the advantages of prolonged-release melatonin and synthetic melatoninergic agonists," 2009, pp. 341-354, Neuropsychiatric Disease and Treatment, Dove Medical Press (NZ) Ltd., vol. 5, No. 1 (XP009137641).
Ockert, "A new dawn in the sleep disorders pipeline?," 2012, pp. 595-596, Nature Reviews, Drug Discovery, vol. 11, No. 8 (XP055057972).
Patent Cooperation Treaty, Notification of Transmittal of the International Search Report and the Written Opinion of the International Searching Authority, or the Declaration for PCT/US2013/023312 dated Jul. 22, 2013, 21 pages.
Lockley et al., "Relationship Between Napping and Melatonin in the Blind," Feb. 1997, pp. 16-25, Journal of Biological Rhythms, vol. 12, No. 4.
Lockley et al., "Sleep and Activity Rhythms are Related to Circadian Phase in the Blind," Jan. 1999, pp. 616-623, Sleep, vol. 22, No. 5.
Lockley et al., "Relationship Between Melatonin Rhythms and Visual Loss in the Blind," Jun. 2010, pp. 3763-3770, Journal of Clinical Endocrinology and Metabolism, vol. 82, No. 11, downloaded from: jcem.endojournals.org.
Shameem, Notice of Allowance and Fee(s) Due for U.S. Appl. No. 13/751,011 dated Jun. 10, 2014, 51 pages.
Pagani, Supportive Information, "Circadian period determination in blind subjects (Guildford)," 2010, 6 pages, Retrieved from: URL: http://www.plosone.org/article/info%3Adoi%2F10.1371%2Fjournal.pone.0013376#s5 (XP055059606).
Pagani et al., "The Physiological Period Length of the Human Circadian Clock In Vivo is Directly Proportional to Period in Human Fibroblasts," 2010, pp. 1-7, PLoS ONE, vol. 5, No. 10.
Vanda Pharmaceuticals, "Efficacy and Safety of Tasimelteon Compared with Placebo in Totally Blind Subjects with Non-24-Hour Sleep-Wake Disorder," 2011, 5 pages, ClincalTrials.gov archive, View of NCT01163032.
Patent Cooperation Treaty, Invitation to Pay Additional Fees and Partial International Search for PCT/US2013/023315 dated Apr. 24, 2013, 12 pages.
Anonymous, "The Japanese Journal of Clinical and Experimental Medicine," Jun. 2012, vol. 89, No. 6, pp. 737-741.
JP Office Action and English Translation thereof for Japanese Patent Application No. P2016-177959 dated Jun. 19, 2018, 13 pages.
Anonymous, "P450 Drug Interaction Table—Department of Medicine at Indiana University," 2013, 4 pages, retrieved from: http://medicine.iupui.edu/clinpharm/ddis/main-tablet.
Vanda Pharmaceuticals, Inc., "Initial Clinical Data Reveal Potential of Tasimelteon to Reset the Body Clock in Non-24-Hour Sleep-Wake Disorder," 2012,4 pages, Investor Relations Press Release.
Patent Cooperation Treaty; The International Search Report and the Written Opinion of the International Searching Authority for PCT/US2013/023315, dated Nov. 17, 2014, 24 pages.
Arendt, "Melatonin and Human Rhythms," Chronobiology International. 23(1&2):21-37 (2006).
Badyal et al., "Cytochrome P450 and Drug Interactions," Indian Journal of Pharmacology. 33:248-59 (2001).
Notice of Opposition for EP Application No. 07797634.8, dated Nov. 2, 2015, 28 pages.
Notice of Opposition for EP Application No. 07797634.8, dated Nov. 3, 2015, 14 pages.
Kippax, "Systematic Method Development for Laser Diffraction Particle Sizing," American Laboratory. Aug. 2004 (4 pages).
Vanda Pharmaceuticals, Inc., "VEC-162: Development Pipeline," www.vandapharmaceuticals.com/development-vec162.html, Apr. 30, 2006, retrieved from http://web.archive.org (3 pages).

(56) References Cited

OTHER PUBLICATIONS

"General Considerations for Clinical Trials," ICH Harmonised Tripartite Guideline, International Conference on Harmonisation of Technical Requirements for Registration of Pharmaceuticals for Human Use. Current Step 4 version, dated Jul. 17, 1997 (17 pages).

Vanda Pharmaceuticals, Inc., "Vanda Pharmaceuticals' VEC-162 Demonstrates Positive Results in a Phase III Transient Insomnia Clinical Trial," Investor Relations—Press Releases, dated Nov. 15, 2006 (3 pages).

Terao et al., "Recent and potential drugs for treatment of insomnia," Folia Pharmacol. Jpn. 129:35-41 (2007) (in Japanese).

Form S-1 Registration Statement under The Securities Act of 1933 (Vanda Pharmaceuticals, Inc.), dated Apr. 7, 2006, pp. 64-65, http://www.nasdaq.com/markets/ipos/filing.ashx?filingid=4083647.

Dalziel, "JPMorgan 24th Annual Healthcare Conference," !IDrugs. 9(3):182-4 (2006).

Office Action for U.S. Appl. No. 14/688,301, dated Mar. 3, 2016, 60 pages.

Starkey et al., "Modulation of the rat suprachiasmatic circadian clock by melatonin in vitro", (1995) Neuroreport 6, 1947-1951.

Stoschitzky et al., "Influence of beta-blockers on melatonin release", (1999) Eur.J Clin Pharmacol. 55,111-115.

Strogatz et al., "Circadian pacemaker interferes with sleep onset at specific times each day: role in insomnia", (1987) Am J Physiol 253, R172-R178.

Turek et al., "Melatonin, sleep, and circadian rhythms: rationale for development of specific melatonin agonists", (2004) Sleep Med 5, 523-532.

Vachharajani et al., "Preclinical pharmacokinetics and metabolism of BMS-214778, a novel melatonin receptor agonist", (2003) J.Pharm. Sci. 92, 760-772.

Rajaratnam et al., "The melatonin agonist VEC-0162 Immediately phase-advances the human circadian system", Jan. 6, 2010, A54.

Van Den Heuvel et al., "Thermoregulatory and soporific effects of very low dose melatonin injection.", (1999) Am J Physiol. 276, E249-254.

Van Someren et al., "Improving melatonin circadian phase estimates", (2007) Sleep Med. 8, 590-601.

Viswanathan et al., "Expression of melatonin receptors in arteries involved in thermoregulation", (1990) Proc. Natl. Acad. Sci U. S. A 87, 6200-6203.

Wright et al., "Intrinsic period and light intensity determine the phase relationship between melatonin and sleep in humans", (2005) J. Biol. Rhythms 20, 168-177.

Wright et al., "Intrinsic near-24-h pacemaker period determines limits of circadian entrainment to a weak synchronizer in humans", (2001) Proc. Natl. Acad. Sci U. S. A 98, 14027-14032.

Wright et al., "Sleep and wakefulness out of phase with internal biological time impairs learning in humans", (2006) J. Cogn Neurosci. 18, 508-521.

Zeitzer et al., "Sensitivity of the human circadian pacemaker to nocturnal light: melatonin phase resetting and suppression", (2000) J Physiol 526 Pt 3, 695-702.

Zeitzer et al., "Absence of detectable melatonin and preservation of cortisol and thyrotropin rhythms in tetraplegia", (2000) J Clin Endocrinol Metab 85, 2189-2196.

Zeitzer et al., "Plasma melatonin rhythms in young and older humans during sleep, sleep deprivation, and wake", (2007) Sleep 30, 1437-1443.

Birznieks et al., "Melatonin Agonist VEC-162 Improves Sleep Onset and Maintenance in a Model of Transient Insomnia", Sleep, vol. 30, Abstract, Supplement, 2007, A264.

Levin, D2, RUAA—101669, May 9, 2012, 2 pgs.

Erman et al., "An efficacy, safety, and dose-response study of Ramelteon in patients with chronic primary insomnia", Sleep Medicine 7, 2006, 17-24.

Feeney et al., "Melatonin agonist tasimelteon improves sleep in primary insomnia characterized by difficulty falling asleep", Sleep, vol. 32, Abstract, Supp. 2009, A43.

"Phase III Data Show Vanda Pharmaceuticals Rasimelteon (VEC-0162) Significantly Improves Sleep in Patients with Chronic Insomnia", A Pharmaceuticals—Inventor Relations Press Release, Jun. 26, 2008, 4 pgs.

Office Action and English Translation thereof for Japanese Patent Application No. P2018-064884 dated Jan. 17, 2019, 6 pages.

Nakamura et al., "Daily melatonin intake resets circadian rhythms of a sighted man with non-24-hour sleep-wake syndrome who lacks the nocturnal melatonin rise," Psychiatry and Clinical Neurosciences, 1997, vol. 51, pp. 121-127.

Tomoda et al., "A school refusal case with biological rhythm disturbance and melatonin therapy," Brain & Development, 1994, vol. 16, pp. 71-76.

Sack et al., "Melatonin Administration to Blind People: Phase Advances and Entrainment," Journal of Biological Rhythms, vol. 6, No. 3, 1991, pp. 249-261.

\* cited by examiner

FIG. 3
Subject: 409-3003
Target Bedtime: 21:00
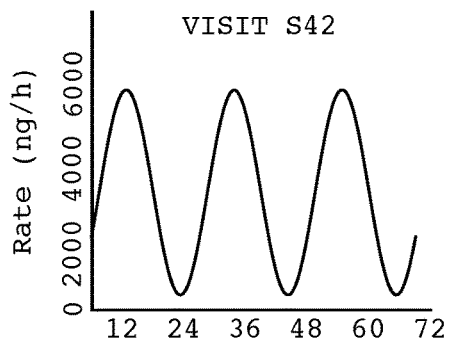
VISIT S42
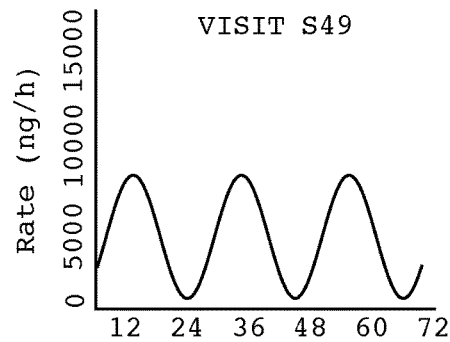
VISIT S49
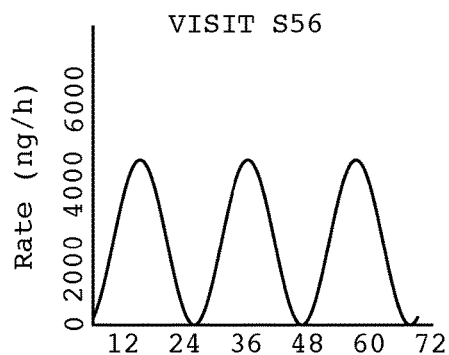
VISIT S56
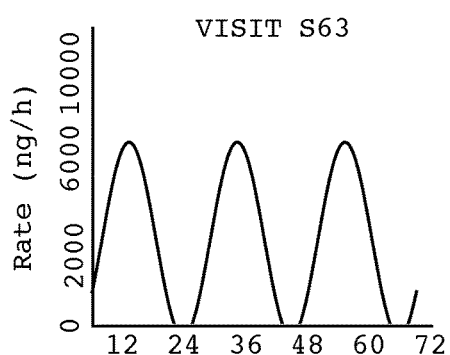
VISIT S63
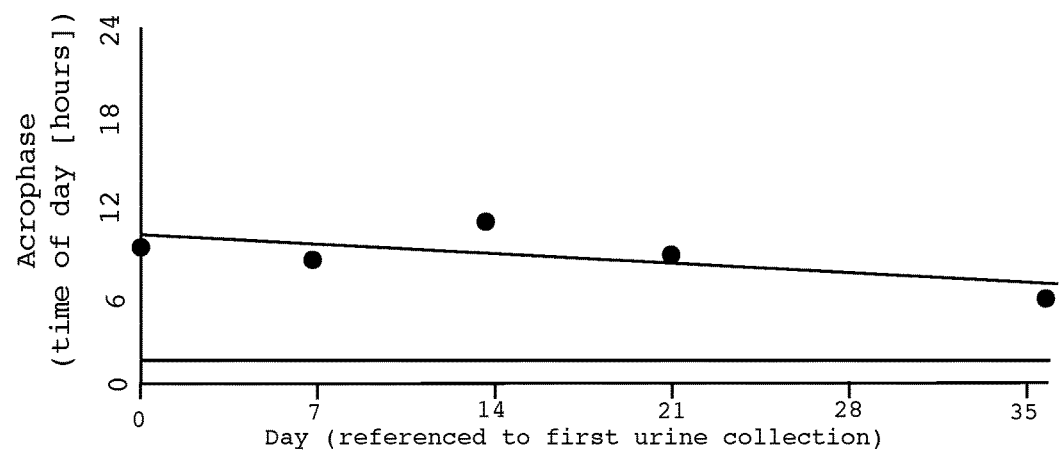

FIG. 4  Subject: 410-3004
Target Bedtime: 23:00
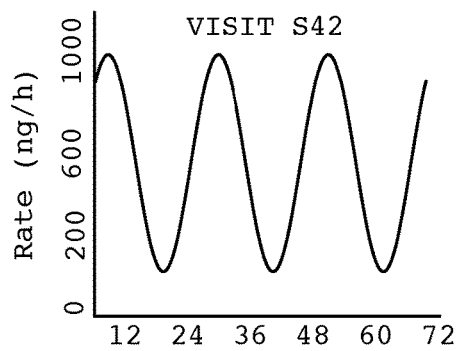
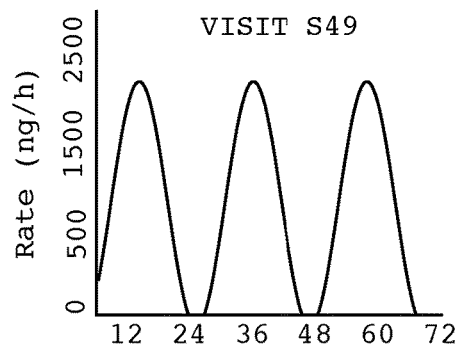
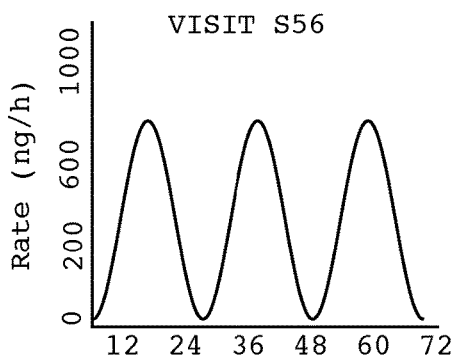
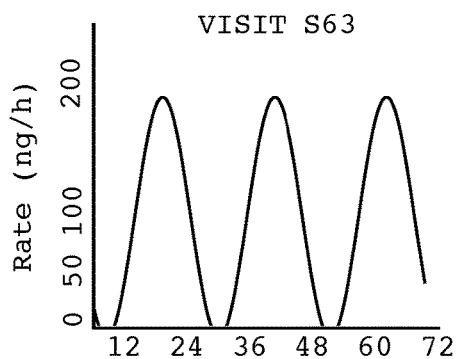
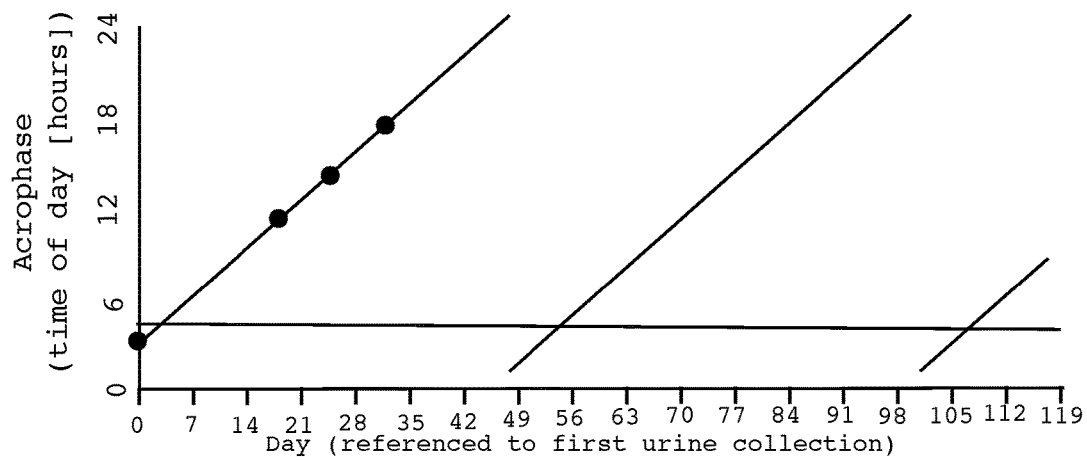

TREATMENT OF CIRCADIAN RHYTHM DISORDERS

CROSS-REFERENCE TO RELATED APPLICATIONS

This application is a continuation of U.S. patent application Ser. No. 15/378,353, filed Dec. 14, 2016, which is a divisional application of U.S. patent application Ser. No. 14/374,257, filed 24 Jul. 2014, now U.S. Pat. No. 9,549,913, which is the US national phase of PCT/US13/23315, filed 25 Jan. 2013, which claims the benefit of U.S. provisional patent application Nos. 61/590,974, filed 26 Jan. 2012, 61/640,067, filed 30 Apr. 2012, 61/650,455, filed 22 May 2012, 61/650,458, filed 22 May 2012, 61/714,149, filed 15 Oct. 2012, 61/738,985, filed 18 Dec. 2012, 61/738,987, filed 18 Dec. 2012, and 61/755,896, filed 23 Jan. 2013, each of which is hereby incorporated herein as though fully set forth.

FIELD OF THE INVENTION

Embodiments of the invention relate generally to the field of circadian rhythm disorders (CRDs) and, more particularly, to the entrainment of circadian rhythms in persons afflicted with Non-24 Hour Disorder (Non-24).

BACKGROUND OF THE INVENTION

The master body clock controls the timing of many aspects of physiology, behavior and metabolism that show daily rhythms, including the sleep-wake cycles, body temperature, alertness and performance, metabolic rhythms and certain hormones which exhibit circadian variation. Outputs from the suprachiasmatic nucleus (SCN) control many endocrine rhythms including those of melatonin secretion by the pineal gland as well as the control of cortisol secretion via effects on the hypothalamus, the pituitary and the adrenal glands. This master body clock, located in the SCN, spontaneously generates rhythms of approximately 24.5 hours. These non-24-hour rhythms are synchronized each day to the 24-hour day-night cycle by light, the primary environmental time cue which is detected by specialized cells in the retina and transmitted to the SCN via the retino-hypothalamic tract. Inability to detect this light signal, as occurs in most totally blind individuals, leads to the inability of the master body clock to be reset daily and maintain entrainment to a 24-hour day.

Non-24-Hour Disorder

Non-24, also referred to as Non-24-Hour Sleep-Wake Disorder (N24HSWD) or Non-24-Hour Disorder, is an orphan indication affecting approximately 65,000 to 95,000 people in the U.S. and 140,000 in Europe. Non-24 occurs when individuals, primarily blind with no light perception, are unable to synchronize their endogenous circadian pacemaker to the 24-hour light/dark cycle. Without light as a synchronizer, and because the period of the internal clock is typically a little longer than 24 hours, individuals with Non-24 experience their circadian drive to initiate sleep drifting later and later each day. Individuals with Non-24 have abnormal night sleep patterns, accompanied by difficulty staying awake during the day. Non-24 leads to significant impairment, with chronic effects impacting the social and occupational functioning of these individuals.

In addition to problems sleeping at the desired time, individuals with Non-24 experience excessive daytime sleepiness that often results in daytime napping.

The severity of nighttime sleep complaints and/or daytime sleepiness complaints varies depending on where in the cycle the individual's body clock is with respect to their social, work, or sleep schedule. The "free running" of the clock results in approximately a 1-4 month repeating cycle, the circadian cycle, where the circadian drive to initiate sleep continually shifts a little each day (about 15 minutes on average) until the cycle repeats itself. Initially, when the circadian cycle becomes desynchronous with the 24 h day-night cycle, individuals with Non-24 have difficulty initiating sleep. As time progresses, the internal circadian rhythms of these individuals becomes 180 degrees out of synchrony with the 24 h day-night cycle, which gradually makes sleeping at night virtually impossible, and leads to extreme sleepiness during daytime hours.

Eventually, the individual's sleep-wake cycle becomes aligned with the night, and "free-running" individuals are able to sleep well during a conventional or socially acceptable time. However, the alignment between the internal circadian rhythm and the 24-hour day-night cycle is only temporary.

In addition to cyclical nighttime sleep and daytime sleepiness problems, this condition can cause deleterious daily shifts in body temperature and hormone secretion, may cause metabolic disruption and is sometimes associated with depressive symptoms and mood disorders.

It is estimated that 50-75% of totally blind people in the United States (approximately 65,000 to 95,000) have Non-24. This condition can also affect sighted people. However, cases are rarely reported in this population, and the true rate of Non-24 in the general population is not known.

The ultimate treatment goal for individuals with Non-24 is to entrain or synchronize their circadian rhythms into an appropriate phase relationship with the 24-hour day so that they will have increased sleepiness during the night and increased wakefulness during the daytime.

Tasimelteon

Tasimelteon is a circadian regulator which binds specifically to two high affinity melatonin receptors, Mel1a (MT1R) and Mel1b (MT2R). These receptors are found in high density in the suprachiasmatic nucleus of the brain (SCN), which is responsible for synchronizing our sleep/wake cycle. Tasimelteon has been shown to improve sleep parameters in prior clinical studies, which simulated a desynchronization of the circadian clock. Tasimelteon has so far been studied in hundreds of individuals and has shown a good tolerability profile.

SUMMARY OF THE INVENTION

Embodiments of the invention relate to the discovery that tasimelteon can be used to treat a free running circadian rhythm, in patients, including light perception impaired patients, e.g., blind patients, in whom such free running circadian rhythm manifests itself as Non-24.

Embodiments of this invention further relate to the invention of a method for determining a person's circadian rhythm (tau) and to the application of such methodology to the treatment of a free running circadian rhythm.

Embodiments of this invention further relate to the treatment of subjects who present with symptoms of Non-24, specifically, e.g., sleep drifting later each day, abnormal night sleep patterns, and/or difficulty staying awake during the day, leading in many cases to significant impairment, with chronic effects impacting the social and occupational functioning of these individuals, as well as possible negative health effects of chronic misalignment.

Thus, in illustrative embodiments, the invention comprises a method of determining the circadian period ($\tau$) in a human subject, said method comprising:
a) collecting at least one biological sample from the patient during each of a plurality of regular collection intervals (CIs) during at least two Collection Sessions, each Collection Session being at least 48 hours in duration;
b) if multiple biological samples are collected during each CI, then optionally physically pooling all samples collected within a given CI and, in such case, assigning a Collection Time Point for each CI;
c) measuring the amount (absolute or concentration) of melatonin or of a melatonin surrogate in each of the samples or pooled samples;
d) optionally converting the amount of melatonin or melatonin surrogate at each Collection Time Point to a rate of production;
e) analyzing the amount of melatonin or melatonin surrogate or the rate of melatonin or melatonin surrogate production at each Collection Time Point to model the patient's cycle, including the acrophase, of melatonin or melatonin surrogate amount or production on each day;
f) fitting serial acrophase determinations to a weighted linear regression model in order to determine $\tau$, wherein $\tau = 24 + \text{slope}$.

A further illustrative embodiment is a method of treating a human patient presenting symptoms of Non-24, said method comprising determining the patient's $\tau$ by the method described above, and further described below, if the patient's $\tau$ is longer than 24 hours, then treating the patient by daily internally administering to the patient an effective amount of a melatonin agonist.

BRIEF DESCRIPTION OF THE FIGURES

FIG. 3 is an example of a patient report for a patient determined not to have a free-running circadian rhythm based on cortisol analyses.

FIG. 4 is an example of a patient report for a patient determined to have a free-running circadian rhythm based on cortisol analyses.

DETAILED DESCRIPTION OF THE INVENTION

Figure 1:
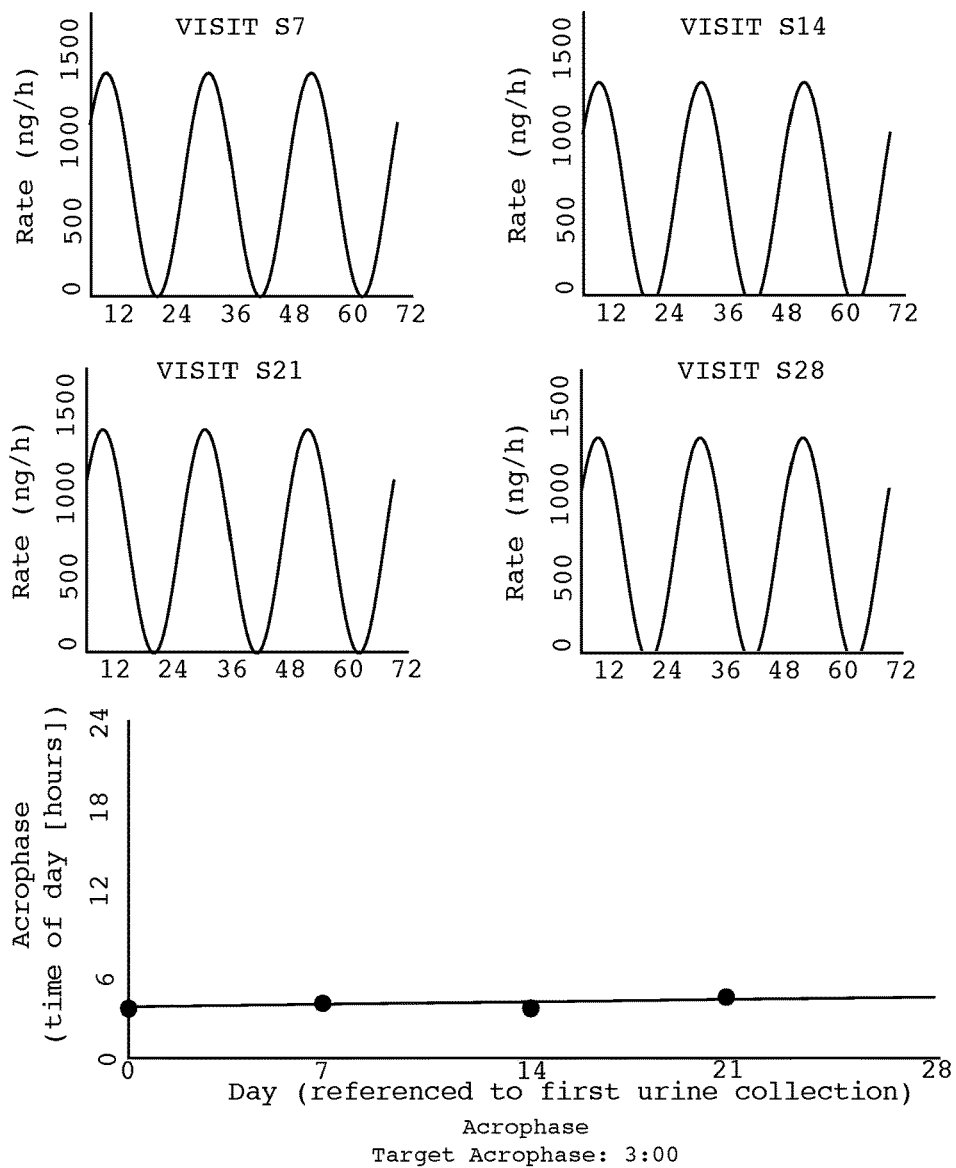
FIG. 1 is an example of a patient report for a patient determined not to have a free-running circadian rhythm based on aMT6s analyses.

Tasimelteon has the chemical name: trans-N-[[(2,3-dihydrobenzofuran-4-yl)cycloprop-lyl]methyl]propanamide, has the structure of Formula I:

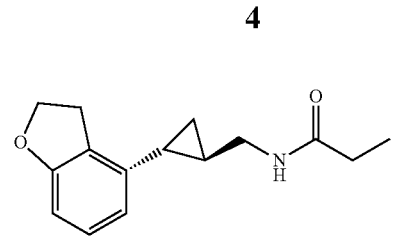

Formula I and is disclosed in U.S. Pat. No. 5,856,529 and US 20090105333, both of which are incorporated herein by reference as though fully set forth.

Tasimelteon is a white to off-white powder with a melting point of about 78° C. (DSC) and is very soluble or freely soluble in 95% ethanol, methanol, acetonitrile, ethyl acetate, isopropanol, polyethylene glycols (PEG-300 and PEG-400), and only slightly soluble in water. The native pH of a saturated solution of tasimelteon in water is 8.5 and its aqueous solubility is practically unaffected by pH. Tasimelteon has 2-4 times greater affinity for MT2R relative to MT1R. It's affinity ($K_i$) for MT1R is 0.3 to 0.4 and for MT2R, 0.1 to 0.2. Tasimelteon is useful in the practice of this invention because it is a melatonin agonist that has been demonstrated, among other activities, to entrain patients suffering from Non-24.

In related aspects, this invention relates to the use of a tasimelteon metabolite as the melatonin agonist. Tasimelteon metabolites include, for example, a phenol-carboxylic acid analog (M9) and a hydroxypropyl-phenol analog (M11). Each is formed in humans following oral administration of tasimelteon.

Specifically, aspects of the invention encompass use of tasimelteon or of compounds of Formulas II or III, including salts, solvates, and hydrates of tasimelteon or of compounds of Formula II or Formula III, in amorphous or crystalline form.

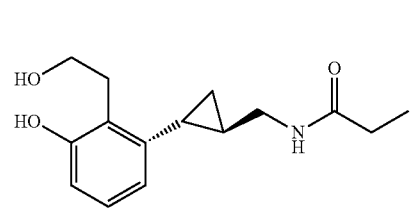

Formula II (M11)

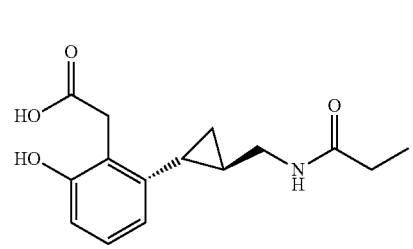

Formula III (M9)

While depicted herein in the R-trans configuration, the invention nevertheless comprises use of stereoisomers thereof, i.e., R-cis, S-trans, and S-cis. In addition, the invention comprises use of prodrugs of tasimelteon or of compounds of Formula II or of Formula III, including, for example, esters of such compounds. The discussion that follows will refer to tasimelteon but it is to be understood that the compounds of Formula II and III are also useful in the practice of aspects of the invention.

Metabolites of tasimelteon include, for example, those described in "Preclinical Pharmacokinetics and Metabolism of BMS-214778, a Novel Melatonin Receptor Agonist" by Vachharajani et al., J. Pharmaceutical Sci., 92(4):760-772, which is hereby incorporated herein by reference. The active metabolites of tasimelteon can also be used in the method of this invention, as can pharmaceutically acceptable salts of tasimelteon or of its active metabolites. For example, in addition to metabolites of Formula II and III, above, metabolites of tasimelteon also include the monohydroxylated analogs M13 of Formula IV, M12 of Formula V, and M14 of Formula VI.

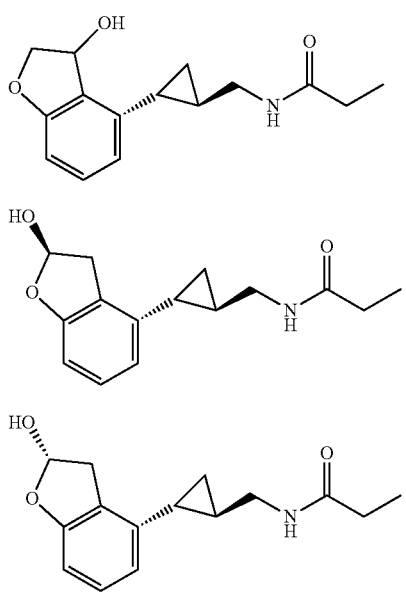

Formula IV

Formula V

Formula VI

Thus, it is apparent that this invention contemplates entrainment of patients suffering free running circadian rhythm to a 24 hour circadian rhythm by administration of a circadian rhythm regulator (i.e., circadian rhythm modifier) capable of phase advancing and/or entraining circadian rhythms, such as a melatonin agonist like tasimelteon or an active metabolite of tasimelteon or a pharmaceutically acceptable salt thereof. Other MT1R and MT2R agonists, i.e., melatonin agonists, can have similar effects on the master body clock. So, for example, this invention further contemplates the use of melatonin agonists such as but not limited to melatonin, N-[1-(2,3-dihydrobenzofuran-4-yl) pyrrolidin-3-yl]-N-ethylurea and structurally related compounds as disclosed in U.S. Pat. No. 6,211,225, LY-156735 ((R)-N-(2-(6-chloro-5-methoxy-1H-indol-3yl)propyl)acetamide) (disclosed in U.S. Pat. No. 4,997,845), agomelatine (N-[2-(7-methoxy-1-naphthyl)ethyl]acetamide) (disclosed in U.S. Pat. No. 5,225,442), ramelteon ((S)-N-[2-(1,6,7,8-tetrahydro-2H-indeno-[5,4-b] furan-8-yl)ethyl]propionamide), 2-phenylmelatonin, 8-M-PDOT, 2-iodomelatonin, and 6-chloromelatonin.

Additional melatonin agonists include, without limitation, those listed in U.S. Patent Application Publication No. 20050164987, which is incorporated herein by reference, specifically: TAK-375 (see Kato, K. et al. Int. J. Neuropsychopharmacol. 2000, 3 (Suppl. 1): Abst P.03.130; see also abstracts P.03.125 and P.03.127), CGP 52608 (1-(3-allyl-4-oxothiazolidine-2-ylidene)-4-methylthiosemicarbazone) (See Missbach et al., J. Biol. Chem. 1996, 271, 13515-22), GR196429 (N-[2-[2,3,7,8-tetrahydro-1H-fur-o(2,3-g)indol-1-yl]ethyl]acetamide) (see Beresford et al., J. Pharmacol. Exp. Ther. 1998, 285, 1239-1245), S20242 (N-[2-(7-methoxy napth-1-yl)ethyl]propionamide) (see Depres-Brummer et al., Eur. J. Pharmacol. 1998, 347, 57-66), S-23478 (see Neuropharmacology July 2000), S24268 (see Naunyn Schmiedebergs Arch. June 2003), S25150 (see Naunyn Schmiedebergs Arch. June 2003), GW-290569, luzindole (2-benzyl-N-acetyltryptamine) (see U.S. Pat. No. 5,093,352), GR135531 (5-methoxycarbonylamino-N-acetyltrypt-amine) (see U.S. Patent Application Publication No. 20010047016), Melatonin Research Compound A, Melatonin Agonist A (see IMSWorld R&D Focus August 2002), Melatonin Analogue B (see Pharmaprojects August 1998), Melatonin Agonist C (see Chem. Pharm. Bull. (Tokyo) January 2002), Melatonin Agonist D (see J. Pineal Research November 2000), Melatonin Agonist E (see Chem. Pharm. Bull. (Tokyo) February 2002), Melatonin Agonist F (see Reprod. Nutr. Dev. May 1999), Melatonin Agonist G (see J. Med. Chem. October 1993), Melatonin Agonist H (see Famaco March 2000), Melatonin Agonist I (see J. Med. Chem. March 2000), Melatonin Analog J (see Bioorg. Med. Chem. Lett. March 2003), Melatonin Analog K (see MedAd News September 2001), Melatonin Analog L, AH-001 (2-acetamido-8-methoxytetralin) (see U.S. Pat. No. 5,151,446), GG-012 (4-methoxy-2-(methylene propylamide)indan) (see Drijfhout et al., Eur. J. Pharmacol. 1999, 382, 157-66), Enol-3-IPA, ML-23 (N-2,4-dinitrophenyl-5-methoxytryptamine) (see U.S. Pat. No. 4,880,826), SL-18.1616, IP-100-9 (U.S. Pat. No. 5,580,878), Sleep Inducing Peptide A, AH-017 (see U.S. Pat. No. 5,151,446), AH-002 (8-methoxy-2-propionamido-tetralin) (see U.S. Pat. No. 5,151,446), and IP-101. Metabolites, prodrugs, stereoisomers, polymorphs, hydrates, solvates, and salts of the above compounds that are directly or indirectly active can, of course, also be used in the practice of this invention.

Melatonin agonists with a MT1R and MT2R binding profile similar to that of tasimelteon, which has 2 to 4 time greater specificity for MT2R, are preferred.

Tasimelteon can be synthesized by procedures known in the art. The preparation of a 4-vinyl -2,3-dihydrobenzofuran cyclopropyl intermediate can be carried out as described in U.S. Pat. No. 7,754,902, which is incorporated herein by reference as though fully set forth.

Pro-drugs, e.g., esters, and pharmaceutically acceptable salts can be prepared by exercise of routine skill in the art.

In patients suffering a Non-24, the melatonin and cortisol circadian rhythms and the natural day/night cycle become desynchronized. For example, in patients suffering from a free-running circadian rhythm, melatonin and cortisol acrophases occur more than 24 hours, e.g., >24.1 hours, prior to each previous days melatonin and cortisol acrophase, respectively, resulting in desynchronization for days, weeks, or even months, depending upon the length of a patient's circadian rhythm, before the melatonin, cortisol, and day/night cycles are again temporarily synchronized.

Chronic misalignment of cortisol has been associated with metabolic, cardiac, cognitive, neurologic, neoplastic, and hormonal disorders. Such disorders include, e.g., obesity, depression, neurological impairments.

This invention shows that entrainment of the melatonin circadian rhythm is linked to entrainment of the cortisol circadian rhythm.

Thus, in one aspect, an illustrative embodiment of the invention provides a method of entraining a patient suffering from an abnormal melatonin circadian rhythm, or an abnormal cortisol circadian rhythm, to a 24 hour circadian rhythm by internally administering to the patient an effective amount of a melatonin agonist, in particular, tasimelteon or an active metabolite thereof.

In related aspects, this invention provides a method of preventing or treating disorders associated with a desynchronous melatonin or cortisol circadian rhythm, i.e., a circadian rhythm that is not synchronized with the natural day/night cycle. Such method comprises internally administering to a patient having a desynchronous melatonin or cortisol circadian rhythm an effective amount of a melatonin agonist, in particular, tasimelteon or an active metabolite thereof, as described in this specification.

The method of treating Non-24 (which includes phase advancing and/or entraining melatonin and/or cortisol circadian rhythm) in a patient suffering therefrom by internally administering an effective amount of tasimelteon as described in this specification tends to be effective more often in patients having higher amounts of endogenous melatonin. In other words, the likelihood of efficacy of treatment is related to the amount of melatonin naturally present in the patient's body.

The method of treating Non-24 (which includes phase advancing melatonin and/or cortisol circadian rhythm) in a patient suffering therefrom by internally administering an effective amount of tasimelteon as described in this specification tends to be effective more often in patients whose pre-treatment circadian rhythm (i.e., tau) is below a certain threshold. Such threshold can be, e.g., 25.0 hours, 24.9 hours, 24.8 hours, 24.7 hours, 24.65 hours, or 24.6 hours, such that the likelihood of efficacy of treatment is greater in the case of patients whose tau is below the threshold.

In accordance with this invention, a regulatory agency, a patient, a healthcare provider, or an insurance provider, or any one or more of such entities or persons, can choose a likelihood of efficacy that is sufficient to support initiation of treatment with a melatonin agonist, in particular, tasimelteon. For example, it may be decided that if the likelihood of efficacy is less than a selected threshold probability, then the patient should not be treated with the melatonin agonist.

Alternatively, such threshold probability can be used as a factor in determining whether or not to apply a heightened standard of monitoring for efficacy and/or adverse events. For example, it may be decided that if the likelihood of efficacy is less than a selected threshold probability, then the patient will be examined for signs of efficacy and/or adverse events within about 6 to 9 weeks following initiation of treatment. Such heightened monitoring can also comprise more frequent monitoring and/or decreased tolerance for lack of apparent efficacy or for occurrence of side effects. For example, if there is no or scant evidence of efficacy or if there are signs of adverse events, perhaps even minor or early signs, then the melatonin agonist treatment may be discontinued or modified. Heightened monitoring may include requiring a patient to maintain a sleep diary which would may include, e.g., the patient's recordation of sleep and wake times, frequency and duration of naps, sleep latency, duration of nighttime sleep, etc., such recordation being, e.g., in writing, digitally, or telephonically.

Efficacy for these purposes can be determined in a number of ways, including, e.g., by determining a patient's tau after initiation of therapy and following at least one complete circadian cycle during which the patient has been treated, e.g., about 6 to about 9 weeks after initiation of therapy, or by examining the patient's physical or emotional health such as by subjecting the patient to a physical examination or to questioning about sleep patterns, side effects, daytime napping, general well-being, etc.

Short of terminating treatment, it may be decided, e.g., that the patient should receive a different dose of the melatonin agonist or a different melatonin agonist, e.g., a different melatonin agonist having the pharmacological activity, i.e., MT1R and MT2R binding and relative binding affinities, and $t_{1/2}$, of tasimelteon.

The threshold probability discussed above can be correlated to a threshold concentration of melatonin in a biological sample taken from a patient. For example, melatonin levels can be directly measured in samples of blood, plasma, urine, saliva, etc., and the melatonin concentration that corresponds to a selected threshold probability can be ascertained. The concentration of melatonin that corresponds to the selected threshold probability can be referred to as the Threshold Concentration.

Melatonin levels are generally determined (1) by measuring the amount of the primary urinary metabolite of melatonin, 6-sulphatoxymelatonin (aMT6s) collected every 2 to 8 hours over a 24 to 48 hour period, (2) by measuring melatonin levels in samples of saliva taken every 30 to 60 minutes under dim light, or (3) by measuring melatonin levels in samples of blood taken frequently, e.g., every 20 to 30 minutes. Such methods are summarized, e.g., by Benloucif et al., J Clin Sleep Med, 4(1): 66-69 (2008).

It is within the skill of the art, and therefore encompassed by this invention, to use any surrogate for melatonin concentrations or rates of production for determining the length of the melatonin rhythm, i.e., tau. For example, as specifically described herein, one may use amounts of aMT6s as a surrogate for amounts of melatonin and one may use the cortisol circadian rhythm or the aMT6s circadian rhythm as a melatonin circadian rhythm surrogate, i.e., the length of the circadian rhythm of cortisol can be a surrogate for the length of the circadian rhythm of aMT6s which can be a surrogate for the length of the melatonin circadian rhythm (i.e. tau). Alternatively or additionally, one may use cortisol as such melatonin surrogate.

In an illustrative embodiment, the amount of melatonin is indirectly measured such as by measuring the amounts of a melatonin surrogate, specifically, aMT6s in urine samples, and using such amounts to estimate acrophase and average and peak endogenous aMT6s amounts or concentrations in blood.

In an illustrative embodiment, the melatonin surrogate is the rate of aMT6s production as ascertained by measuring aMT6s in urine samples. In such case, the Threshold Concentration would actually be a rate of excretion expressed, e.g., in units of ng/hr. Such rate can be determined by measuring the concentration of aMT6s in an aliquot of urine (ng/ml) and multiplying it by volume/time (ml/hr) of the total urinary void from which the aliquot was derived, as more fully explained below. This surrogate measure is used in this illustrative embodiment for convenience only and it can readily be re-calculated as the concentration of aMT6s in urine and expressed, e.g., in ng/ml units or as the absolute amount of aMT6s in urine and expressed, e.g., in ng or mg units. Such amounts, whether expressed as excretion rates, concentrations, or weights, can also be converted into similarly expressed amounts of melatonin.

For example, a patient having a peak aMT6s production rate, i.e., excretion rate, of 1500 ng/hr in urine is a likely responder to tasimelteon. Therefore, the Threshold Concentration can be set at 1500 ng/hr aMT6s. Alternatively, the Threshold Concentration can also be set at 2000 ng/hr of urinary aMT6s (e.g., urine samples collected in 4 hour intervals and during a nighttime sleep period) or any convenient number therebetween, e.g., 1550, 1600, 1650, 1700, 1750, 1800, 1850, 1900, or 1950 ng/hr. Alternatively, the Threshold Concentration can also be set at greater than 2000 ng/hr of urinary aMT6s, e.g., 2100, 2200, 2300, 2400 or 2500 ng/hr.

A Threshold Concentration of 1500 ng/hr aMT6s is indicative of a greater than 50% probability that a given patient will respond to treatment, i.e., greater than 50% of a population of patients having a peak aMT6s concentration in urine (or the melatonin concentration that is equivalent thereto in another biological sample) are expected to respond to treatment. Based on the study results reported above, it is expected that more than about 75%, or even more than about 80% or 90% of patients will respond if they have peak aMT6s production rates in urine (or corresponding melatonin concentrations in a biological sample) of 1500 ng/hr or 2000 ng/hr.

If endogenous melatonin levels are used to predict likelihood of patient response and not for tau determination, then it is not necessary to determine the rate of aMT6s excretion at time points, or spans of timepoints, throughout a full day. Instead, e.g., the amount of melatonin, as inferred from aMT6s in urine, can be measured in urine collected and pooled in a single batch over a 24 hour period or even during a shorter period. Indeed, in illustrative embodiments, melatonin levels as indicated by aMT6s in urine or directly as melatonin in, e.g., blood or saliva, can be measured at given time points once or multiple times per day.

The ability to predict likelihood of response to drug is very important to healthcare providers, e.g., physicians and patients, as well as to healthcare reimbursement providers, e.g., providers of prescription drug insurance. Thus, in one embodiment, prior to initiation of treatment of Non-24 with a melatonin agonist, e.g., tasimelteon, the patient is tested to determine his or her endogenous melatonin levels, in particular, his or her peak melatonin concentration. Such testing can be carried out using a biological sample, e.g., urine, blood, plasma, or saliva using the methodologies described above or any other methodology. Because the method of this invention provides a probability of response, the method of determining peak melatonin concentration does not require precision. It is enough that it provide an estimate within, e.g., 20%, in which case, if the Threshold Concentration is set at 2000 ng/hr urinary aMT6s, a patient would be regarded as a likely responder if the patient's peak aMT6s excretion in urine is determined to be 1600 ng/hr or higher. Even less precision, e.g., within 25% or 30%, may be acceptable. As in the case of determining tau, other surrogates for endogenous melatonin levels can also be used.

A further aspect of this invention arises from the fact that certain therapeutic agents are known to reduce endogenous levels of melatonin. Prominent among such agents are beta-adrenergic receptor antagonists, commonly referred to as "beta blockers", which are commonly prescribed for treatment of cardiac arrhythmias, myocardial infarction, congestive heart failure, and hypertension. Beta blockers include, e.g., alprenolol, altenolol, carvedilol, metoprolol, and propanolol, to name a few.

Thus, in one aspect, this invention comprises classifying Non-24 patients who are receiving beta blocker therapy as poor responders to melatonin agonist therapy. In this illustrative embodiment, such patients may not be subjected to a determination of peak melatonin concentration but, instead, may be treated as if their melatonin concentrations are below a Threshold Concentration. Other factors that may have an adverse effect on efficacy are NSAIDs and light.

In a related illustrative embodiment, a Non-24 patient may be directed to submit to a determination of melatonin concentration because he or she is being treated with beta blocker therapy to ascertain whether or not the beta blocker therapy is in fact causing the patient's peak melatonin level to drop below a Threshold Concentration.

In related aspects of this invention, plasma melatonin levels or beta blocker therapy, or both, are used as efficacy predictors in combination with other markers of efficacy or adverse events. So, for example, an illustrative embodiment of this invention comprises treating a patient suffering from Non-24 with tasimelteon if the patient has peak melatonin levels corresponding to 1500 ng/hr (or 2000 ng/hr) of aMT6s in urine collected during 4 hour periods or a nighttime sleep period and if the patient is positive for one or more additional efficacy markers. Incorporation of such additional efficacy marker or markers can enhance the ability of a healthcare provider to assess the likelihood that a patient suffering a non-24 hour circadian rhythm will benefit from treatment with a melatonin agonist such as tasimelteon.

In related embodiments, a computer-based system receives information about a prescription for tasimelteon and operates to associate that information with information about the patient's endogenous melatonin levels to output a report indicating a probability of efficacy or to output a report stating that a higher or lower dose of tasimelteon, e.g, <20 mg/d or >20 mg/d, is indicated.

Patients can be diagnosed as suffering from Non-24 by estimating each patient's circadian period (tau). Patients whose tau exceeds 24 hours are diagnosed as having Non-24. Thus, in general, Non-24 patients who can benefit from treatment with tasimelteon have a tau, such as may be determined by analyzing the aMT6s or cortisol circadian rhythm, that is longer than 24 hours, e.g., greater than about 0.1 hours longer than 24 hours and in some cases, at least about 0.2, 0.3, 0.4 and as large as about 1.4 hours longer than 24 hours. As discussed herein, the cortisol circadian rhythm can be used in place of or in addition to the aMT6s rhythm, although cortisol circadian rhythm calculations may be slightly less precise in the sense that such data compiled from analyses of a population of patients may exhibit a larger standard deviation.

To monitor circulating melatonin cycles in a subject, it is convenient to assay for levels of the major metabolite of melatonin, which is 6-sulfatoxymelatonin (aMT6s) in urine, as its pattern of production correlates closely with circulating melatonin levels. However, this invention contemplates measurement of aMT6s levels in other bodily samples such as blood, e.g., plasma, or saliva and it also contemplates direct measurement of melatonin or of other surrogates for melatonin levels. It is within the skill of the art to correlate levels of tasimelteon or tasimelteon metabolites in other bodily samples (i.e., other than aMT6s in urine) with circulating melatonin levels. For example, the amounts of cortisol in blood or urine can be used in a manner similar to the use of aMT6s to determine tau.

A useful protocol for estimating tau in candidates for clinical testing for treatment of Non-24, which method can be applied to diagnosis of Non-24 in a given patient, is as follows:

Each subject will undergo four 48-hour urine collection sessions at nominal days 7, 14, 21, and 28. During each session, the start of the session and the time of each void will be recorded. Urine collected over periods of 4 hours (with the first 4 hour collection period of the day beginning at scheduled wake time), or about 8 hours during sleep, will be pooled (the "collection interval"); thus, subjects will have a total of 10 urine collection intervals during each 48-hour period. A study nurse will determine the volume of urine collected during each interval (urine will be transferred to a graduated cylinder) and an aliquot will be assayed for aMT6s.

For each collection interval, the start and end time of the interval will be used to determine the midpoint and duration of the interval. The start time of a given interval is defined as the last void time from the prior 4 hour (or 8 hour) collection interval; the end time of a given interval is defined as the last void time within the collection interval.

The mass of the primary melatonin metabolite (aMT6s) excreted during the interval will be determined as the product of aMT6s concentration and volume of urine. Rate of aMT6s excretion will be determined as the mass of aMT6s excreted divided by the duration of the interval. This rate will be associated with the midpoint of the interval, referenced to the midnight preceding the start of the first interval in that session.

For example, if a collection interval on Day 27 runs from 9 AM to 1 PM (and the patient had a void at exactly 9 AM and a void at exactly 1 PM), midpoint of that interval would be assigned the value 11.0. A comparable interval on the next day of that session would be assigned a value 35.0.

To accommodate changes in the clock time due to Daylight Savings Time changes, no urine collections will occur on a day that the clock changes. For screening there will be occasions when the 4 different weeks that urine collections are conducted will span a change in the clock time. Therefore, all urine collection times will be automatically translated into local standard time for calculations and then translated back to DST for reporting purposes, if appropriate.

In certain situations, urine collections or their recording will be incomplete. The following procedures will be invoked to address this:

1. If a subject fails to timestamp a void, no action will be taken if there are multiple voids with timestamps within one interval.
2. If there is only one void in a collection interval, and the patient cannot recall the time of the void then the entire 48 hour collection period will be excluded from the analysis and the subject will be requested to collect an additional 48 hours of urine after Day 28. It would not be possible to accurately determine to which collection interval the unmarked urine belongs. Consequently, the appropriate assignment of start and stop times to all of the collection intervals would be questionable.
3. If a void is discarded by the patient but the time of the void is known, duration associated with that void (time of the void minus the time of the previous void) will be subtracted from the total duration associated with that interval. This modified duration will be used to calculate rate of aMT6s excretion. If a discarded sample is either the first or last of the samples in an interval, the midpoint of that interval will be calculated without considering that sample.
4. If fewer than 4 samples are available for one 48-hour collection session, fitting of the cosine will be compromised (inadequate degrees of freedom). Consequently, acrophase will not be determined if fewer than four samples are available.

For each session, acrophase will be determined by fitting a cosine to the data from that session using unweighted non-linear regression. Fitting will be performed using a non-linear least squares fitting algorithm. The fitting process will estimate phase shift, mesor, and amplitude and their respective standard errors; period of the cosine will be fixed to 24 hours.[1]*

[1] Although these subjects are presumed to have a tau >24 hours, attempts to estimate tau led to consistently poor results with multiple test datasets. Steven Lockley, Ph.D., an expert in the field uses this approach.

Acrophase will be determined as the phase shift modulus 24 hours.

If acrophase values are available for three or more sessions, tau will be calculated using the following procedure:

1. Acrophase will be recalculated relative to day 0 (24·start day for each session+acrophase).
2. These values will be regressed against start day for each session using weighted linear regression. Weighting will be by the inverse square of the standard error associated with the estimate for acrophase for each session.

Thus, related to this invention is a method for determining a patient's circadian rhythm (tau) and for treating a patient with a melatonin agonist, in particular, tasimelteon, based on that patient's tau. In illustrative embodiments, the method of determining tau and treating a patient based on the patient's tau, in particular, based upon time of aMT6s acrophase, comprises steps (a) through (f), as follows:

a) collecting at least one biological sample from the patient during each of a plurality of regular collection intervals (CIs) during at least two Collection Sessions, each Collection Session being at least 48 hours in duration;

b) if multiple biological samples (i.e., samples of the same type) are collected during each CI, then optionally physically pooling all samples collected within a given CI and, in such case, assigning a Collection Time Point for each CI;

c) measuring the amount (absolute or concentration) of melatonin or of a melatonin surrogate in each of the samples or pooled samples;

d) optionally converting the amount of melatonin or melatonin surrogate at each Collection Time Point to a rate of production;

e) subjecting the amount of melatonin or melatonin surrogate or the rate of melatonin or melatonin surrogate production at each Collection Time Point to cosinor analysis to model the patient's cycle, including the acrophase, of melatonin or melatonin surrogate amount or production on each day;

f) fitting serial acrophase determinations to a weighted linear regression model in order to determine tau ($\tau$), wherein $\tau=24+\text{slope}$.

While cosinor analysis is mentioned above, it will be appreciated that other methods can be used, e.g., a 2-harmonic fit analysis, in particular, for cortisol rhythm analysis.

Following such determination of $\tau$, a patient can be treated with a melatonin agonist, e.g., tasimelteon, such as described in step (g), as follows:

g) if the patient's $\tau$ is longer than 24 hours, then:
   (i) projecting the patient's acrophase for each of at least 30 days following Day 2 of the final Collection Session by adding $\tau$ to the acrophase of said final Day 2 and to each day thereafter and (ii) treating the patient by daily internally administering to the patient an effective amount of the melatonin agonist prior to sleep time, beginning on the night of the Optimal Treatment Initiation Day, or on a night within the Optimal Treatment Initiation Window, during a succeeding circadian cycle.

The Optimal Treatment Initiation Day is the day on which the patient's sleep time is expected to be closest to what it would be if the patient had a normal, i.e., 24 hour, i.e., <24.1 hr, tau. Such day is generally the day of the night on which the patient's melatonin (or melatonin surrogate) acrophase is projected to be the optimal acrophase, i.e., the time at which acrophase would occur if the patient had a normal circadian rhythm. It is not necessary to initiate treatment precisely on the Optimal Treatment Initiation Day but it is recommended that treatment be initiated on such day or within a range of days on either side of such day, said range being referred to herein as the Optimal Treatment Initiation Window. Said window generally comprises the Optimal Treatment Initiation Day and (a) the immediately following days on which the melatonin (or surrogate) acrophase is projected to occur no later than about 3.5 hours (e.g., 3 hours, 3.5 hours or 4 hours) later than the optimal melatonin (or surrogate) acrophase and (b) the immediately preceding days on which melatonin (or surrogate) acrophase is projected to occur no earlier than 5 hours earlier than the optimal melatonin (or surrogate) acrophase.

Figure 2:
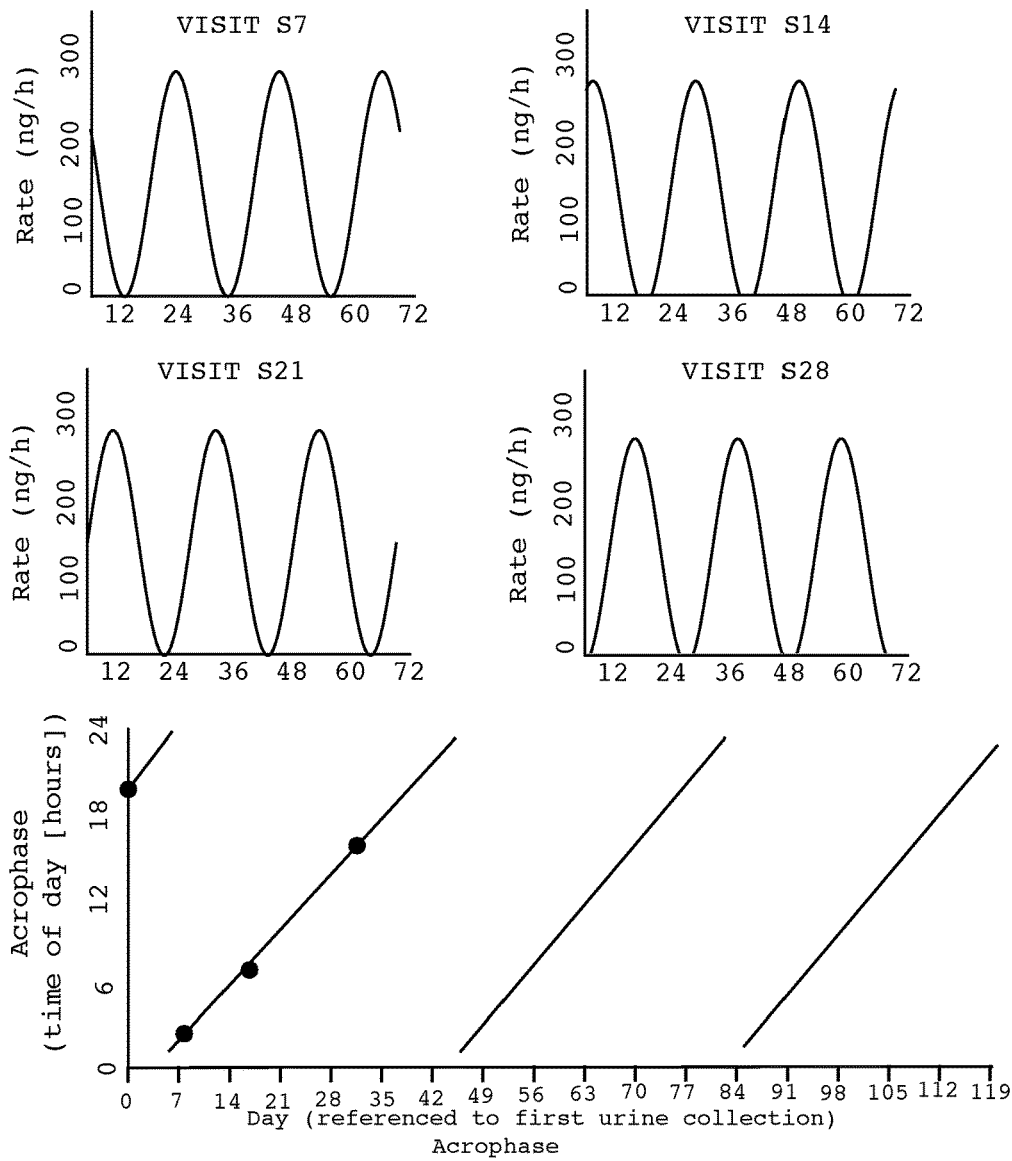
FIG. 2 is an example of a patient report for a patient determined to have a free-running circadian rhythm based on aMT6s analyses.

For the sake of convenience, the Optimal Treatment Initiation Window can be conveniently defined as a set number of days before and after the projected Optimal Treatment Initiation Day, e.g., 2 days before and 2 days after, for a defined Optimal Treatment Initiation Window comprising a total of 5 days. Such window is illustrated in FIG. 2 wherein the first Optimal Treatment Initiation Day is Dec. 4, 2010 and the Optimal Treatment Initiation Window is defined for convenience as Dec. 2, 2010 to Dec. 6, 2010.

It will be appreciated, however, that the window can be customized as summarized above based on a given patient's tau, i.e., depending upon how fast a patient's circadian rhythm is running, such that a patient with a relatively fast-moving circadian rhythm will have a narrower optimal window than a patient with a relatively slow-moving circadian rhythm.

Normal monitoring can comprise step (h), as follows:

h) following a treatment period of at least one complete circadian cycle (based on the patient's pre-treatment tau) assessing entrainment as follows:
(i) If $\tau$ is <24.1 hours with a 95% Confidence Interval that crosses 24.0 hours, then the patient is considered to be entrained to a 24 hour day;
(ii) If the last two acrophase estimates are within the target range, i.e., −2 to +6 hours from optimal acrophase, and the Standard Deviations of these two acrophases overlap, then, taking an additional biological sample collection and re-calculating $\tau$ based on the last three acrophase estimates (the original two+the additional) and if tau is <24.1 hours with a 95% Confidence Interval that crosses 24.0 hours, the patient is considered to be entrained to a 24 hour day;
(iii) If $\tau$>=24.1 hours or the 95% Confidence Interval does not cross 24.0 hours, then the patient is retested.

The duration of a complete circadian cycle will vary depending upon the rate at which a given patient is free running. For example, with reference to FIG. 2, a patient having a tau of 24.6 hours will complete a circadian cycle in approximately 39 days (e.g., Dec. 4, 2010 to Jan. 13, 2011). A patient with a slower rhythm, e.g., tau=24.5, will have a longer cycle and, conversely, a patient with a faster rhythm, e.g., tau=24.7, will have a shorter cycle.

The tau determination and treatment method generally described above can comprise any one or any combination of any two or more of the following limitations:

1. melatonin amounts are indirectly measured by measuring the amounts of a melatonin surrogate, said surrogate being aMT6s.

2. the biological sample is urine, all urine collected during a given CI is physically pooled, and the mid-point of the CI is assigned as the Collection Time Point for that CI.

3. each CI during wake time is 4 hours and sleep time is a single CI, provided that samples are not collected during the first four hour period of each Collection Session or, if collected, are not used in the determination of tau.

4. the Collection Time Point for each CI is defined as the mid-point between the time of the last urine void in the CI immediately preceding a given CI and the last urine void in the given CI.

5. there are 4 Collection Sessions.

6. there are 48 hours in each Collection Session.

7. Collection Sessions are conducted once per week.

8. the Optimal Treatment Initiation Day is the day of the night on which the melatonin or melatonin surrogate acrophase is projected to be the optimal acrophase.

9. the optimal acrophase is the time at which aMT6s acrophase is projected to be closest to and no later than about 3.5 hours prior to the patient's target wake time.

10. the Optimal Treatment Initiation Window comprises the Optimal Treatment Initiation Day and (a) the immediately following days on which the melatonin acrophase is projected to occur no later than 3 hours later than the optimal acrophase and (b) the immediately preceding days on which melatonin acrophase is projected to occur no earlier than 5 hours earlier than the optimal acrophase. In such embodiments, cortisol can be used in place of aMT6s with adjustment to account for the difference between the cortisol circadian rhythm and the aMT6s circadian rhythm.

11. treatment comprises internal administration of an effective amount of tasimelteon once per day, the time of administration being about 5 hours prior to the time of the optimal aMT6s acrophase, and wherein treatment is continued daily for at least one complete circadian cycle. In such embodiments, cortisol can be used in place of aMT6s with adjustment to account for the difference between the cortisol circadian rhythm and the aMT6s circadian rhythm.

12. the amounts of melatonin or melatonin surrogate are measured in absolute units or in concentration units.

13. the amount of melatonin or melatonin surrogate in the biological sample is determined as the product of the aMT6s concentration (mass/volume) and the volume of the biological sample.

14. the rate of melatonin or melatonin surrogate production is determined as the mass of melatonin or melatonin surrogate produced and collected during each CI divided by the duration of the CI.

15. the rate of production is expressed as g/hr.

16. no samples are collected on a day that the clock changes to or from Daylight Savings Time (DST) and, if the Collection Sessions span a change in the clock time, all Collection Time Points are translated into local standard time for calculations and then translated back to DST or standard time, as appropriate, for reporting purposes.

17. samples are collected in a sample collection container by the patient and provided to a laboratory for analysis, e.g., a diagnostic laboratory.

18. the patient records the date and time of each sample collection on a label that has been previously fixed to the collection container or that is applied to the collection container by the patient.

19. the date and time of each collection are printed onto the label by timestamp clock.

20. the biological sample is urine and melatonin amounts are indirectly measured by measuring the amounts of aMT6s and wherein if urine collections or their recordings are incomplete, then:

(i) if a patient fails to timestamp a void, no action is taken if there are multiple voids with timestamps within one CI;

(ii) if there is only one void in a CI and the patient cannot recall the time of the void, then the entire 48 hour Collection Session is excluded from the analysis and an additional Collection Session is conducted;

(iii) if a void is discarded by the patient but the time of the void is known, the duration associated with that void (time of the void minus the time of the previous void) is subtracted from the total duration associated with that CI and the modified duration is used to calculate the rate of aMT6s production but if a discarded sample is either the first or last of the samples in a given CI, then the midpoint of that CI will be calculated without considering that sample; provided that, if fewer than 4 samples are available for any one Collection Session, acrophase will not be determined for that Collection Session.

21. in step (h), if $\tau >= 24.1$ hours or the 95% Confidence Interval does not cross 24.0 hours, then treatment is continued and the patient is retested after a second complete circadian cycle.

22. in step (g), if the patient's $\tau$ is longer than 24 hours, e.g., $\tau >= 24.1$ hours, the patient's acrophase is projected for each of the 90 days following Day 2 of the final Collection Session.

23. aMT6s or cortisol is extracted from pooled urine samples by solid phase extraction, the extracts are evaporated to dryness, the residue is then reconstituted with solvent, and the solution is analyzed by HPLC-MS, an antibody binding assay, or other analytical technique. Thus, a particular illustrative embodiment of a method of determining tau and thereafter treating a patient thereby determined to have a free-running circadian rhythm is as follows:

a) collecting and, if more than one, physically pooling urine samples from the patient during each of 9 Collection Intervals (CIs) during four weekly 48 hour collection sessions, said 9 CIs being CI2, CI3, CI4, CI5, CI6, CI7, CI8, CI9, and CI10, as follows:

CI1: 4 hour period beginning approximately on initiation of wake time of Day 1 of the first Collection Session;

CI2: 4 hour period beginning at the end of CI1;
CI3: 4 hour period beginning at the end of CI2;
CI4: 4 hour period beginning at the end of CI3;
CI5: Overnight, i.e., sleep time (approx 8 hours),
CI6: 4 hour period beginning approximately on initiation of wake time of Day 2 of the collection session;
CI7: 4 hour period beginning at the end of CI6;
CI8: 4 hour period beginning at the end of CI7;
CI9: 4 hour period beginning at the end of CI8;
CI10: Overnight, i.e., sleep time (approx 8 hours), b) (i) optionally collecting and discarding samples during CI1 and (ii) assigning the mid-point between the last void of each CI immediately preceding a given subsequent CI and the last void of the given subsequent CI as the Collection Time Point for each of CI2, CI3, CI4, CI5, CI6, CI7, CI8, CI9, and CI10;

c) measuring the amount of aMT6s or cortisol in each of the ten samples;

d) converting the measured amount of aMT6s or cortisol at each Collection Time Point to a rate of production;

e) subjecting the rate of aMT6s or cortisol production rate at each Collection Time Point to cosinor analysis to model the cycles, including the acrophase, of aMT6s or cortisol production on each day;

f) fitting serial acrophase determinations to a weighted linear regression model in order to determine circadian period ($\tau$), wherein $\tau = 24 + \text{slope}$ ($p </= 0.05$);

g) if the patient's $\tau$ is longer than 24 hours, then:

(i) projecting the patient's acrophase for each of the 90 days following Day 2 of the final Collection Session by adding $\tau$ to the acrophase of said final Day 2 and to each day thereafter and (ii) treating the patient by daily internally administering to the patient an effective amount of tasimelteon prior to sleep time, beginning on the night of the Optimal Treatment Initiation Day, or on a different night within the Optimal Treatment Initiation Window, during the next succeeding circadian cycle h) following a treatment period of one complete circadian cycle, assessing entrainment as follows:

(i) if $\tau$ is <24.1 hours with a 95% Confidence Interval that crosses 24.0 hours, then the patient is considered to be entrained to a 24 hour day;

(ii) if the last two acrophase estimates are within the target range, i.e., −2 to +6 hours from optimal acrophase, and the Standard Deviations of these two acrophases overlap, then, taking an additional 48-hour urine collection and recalculating $\tau$ based on the last three acrophase estimates (the original two+the additional) and if tau is <24.1 hours with a 95% Confidence Interval that crosses 24.0 hours, the patient is considered to be entrained to a 24 hour day;

(iii) if $\tau >= 24.1$ hours or the 95% Confidence Interval does not cross 24.0 hours, then the patient is retested with an additional four 48-hour urine collection scheduled beginning 1 circadian cycle from the first collection.

It will be apparent that in the urine collection and analysis methods that may be used in the practice of aspects of this invention, it is not essential to use the entire volume of urine collected during each Collection Interval.

The method of treatment of Non-24 by internally administering an effective amount of a melatonin agonist, in particular, tasimelteon, is not dependent upon the method for diagnosing or monitoring patients. Instead, said method of treatment is useful in treating Non-24 patients regardless of how diagnosed. Similarly, other markers may be used to predict urinary aMT6s or cortisol acrophase.

Non-entrained persons, i.e., persons with a non-24 hour circadian rhythm, may exhibit symptoms of Non-24 with a clearly non-24 hour sleep period such that initiation of sleep and waking times, unless artificially interrupted, begin later each succeeding day. Other patients may exhibit less severe shifts in sleep period and a significant number may exhibit no shift in sleep period. Such patients, particularly those who do not exhibit shift in sleep period, can be misdiagnosed as having a normal tau if the diagnosis is based solely on sleep and wake times. Some patients that exhibit mild or no shift in sleep period may have cyclic patterns of one or more of sleep latency, nighttime sleep duration and daytime naps. Regardless of the sleep problem, patients with non-24 hour circadian rhythms may be at risk for other circadian-related disorders, for example, metabolic disorders.

Entrainment of patients diagnosed as suffering from a non-24 hour circadian rhythm, including Non-24, can be effected by initiating internal administration of a melatonin agonist like tasimelteon or an active metabolite of tasimelteon or a pharmaceutically acceptable salt thereof, at any time or treatment can be initiated on or about a day on which the patient's melatonin acrophase (based, e.g., on urinary aMT6s acrophase) is predicted to occur about 3 to 4 hours, or about 3.5 hours, e.g., 3.25 hrs to 3.75 hrs, prior to a target wake time selected for or by a given patient. The "ideal" day for initiation of treatment can be more explicitly defined as the day when the subject's predicted acrophase is both 1) closest to 3.5 hours prior to target wake time and 2) earlier than that time. The latter qualifier makes it more likely than not that treatment initiation will occur in a phase-advance part of the phase response curve.

For example, treatment of a patient who has a target bedtime of 10:00 p.m. and a target wake time of 7:00 a.m., treatment initiation can be on a day when urinary aMT6s acrophase is predicted to occur at 3:30 am. However, treatment with tasimelteon can conveniently be initiated on a day on which melatonin acrophase, e.g., using calculated urinary aMT6s acrophase, is predicted to be between about 5.5 hours before target wake time and 2.5 hours after target wake time. Without intending to be bound to a particular theory, this flexibility is apparently owing to the unusually marked effects of such active ingredient on circadian rhythm upon initiation of treatment (e.g., phase advance by as much as about 5 hours on initial treatment).

If a marker for circulating melatonin levels other than urinary aMT6s is employed, e.g., aMT6s in plasma, then the above times would be adjusted accordingly but would nevertheless be indirectly indicative of urinary aMT6s levels.

In patients suffering Non-24, a calendar day may not be associated with an acrophase. For example, if a subject's tau is 24.5 hours and acrophase occurs at 23:45 (11:45 pm) on 28 August, the next acrophase is predicted to occur at 00:15 (12:15 am) on 30 August.

In addition to entraining a Non-24 patient's tau to 24 hours, e.g., <24.1 hours, a melatonin agonist, in particular, tasimelteon, can also increase total sleep time per day and reduce total nap time per day.

Entrainment of a patient can be determined by various methods, including by determining the patient's tau by the above-described or different methodologies. In addition, or alternatively, a patient's or a healthcare worker's perception of improvement can be assessed such as by use of a questionnaire. Such perception could utilize, e.g., the Clinical Global Impression of Change (CGI-C), The CGI-C is a healthcare worker-rated assessment of change in global clinical status, defined as a sense of well-being and ability to function in daily activities. See, e.g., Lehmann E., Pharmacopsychiatry 1984, 17:71-75. It is a 7 point rating scale whereby clinicians, physicians, or other healthcare workers rate a patient's improvement in symptoms relative to the start of the study. It is rated as: 1, very much improved; 2, much improved; 3, minimally improved; 4, no change; 5, minimally worse; 6, much worse; or 7, very much worse.

The questionnaire can be administered prior to or early following initiation of treatment, e.g., prior to Day 1 or, e.g., on Day 56 (counted from first day of treatment) and it can be re-administered later following initiation of treatment, e.g., Day 112 and/or Day 183.

Due to the cyclicality of Non-24, a patient's overall improvement should not be assessed at one time-point/visit. Consequently, the average score of CGI-C in the last two scheduled assessments (e.g., Day 112 and Day 183) can be used to evaluate the patient's overall improvement.

In addition to or as an alternative to measuring a patient's tau following a period of treatment and/or utilizing patient or healthcare worker assessment such as by use of the CGI-C, various sleep parameters can also be used to assess efficacy of treatment, i.e., entrainment.

For example, sleep parameters that can be assessed include one or more of Lower Quartile of Nights of nTST (LQ-nTST), Upper Quartile of Days of dTSD (UQ-dTSD), and Midpoint of Sleep Timing (MoST).

Lower Quartile of Nights of nTST (LQ-nTST)

Patients suffering from Non-24 may have trouble sleeping as a result of their sleep cycle being out of synchrony with the 24 hour clock. This leads to intervals of poor sleep followed by intervals of good sleep. Therefore, the severity of symptoms associated with Non-24 is best illustrated when isolating the worst nights of sleep and the days with the most naps. Evaluating the 25% worst nights of sleep of an individual serves as a good measure of how an individual is suffering from this circadian disease in relationship to nighttime total sleep time (nTST).

The method for calculating the LQ-nTST is described as follows. For a given individual, all non-missing values (must include >70% of one circadian cycle for both baseline and randomized data) of nighttime total sleep time are ordered from smallest to largest. The first 25% (ceiling(number of non-missing records)/4) of the records are flagged as belonging to the lower quartile of nighttime total sleep time. The average of these values is calculated and this result is denoted LQ-nTST.

For example, assume that a subject has 21 nTST baseline records: 6.75, 6.75, 1, 1, 6.75, 1.083, 7.167, 0.833, 7.083, 7.983, 7, 7, 7.833, 7, 7.667, 7.183, 7, 7.067, 7, 7.183, and 7.

These are rank ordered and the first 25% of records are selected [(21/4) =6]: 0.833, 1, 1, 1.083, 6.75, and 6.75.

Those values are averaged to obtain the subject's LQ-nTST: (0.833+1+1+1.083+6.75+6.75)/6=2.91.

Upper Quartile of Days of dTSD (UQ-dTSD)

Patients suffering from Non-24 have a propensity to sleep during the day as a result of their sleep cycle being out of synchrony with a 24 hour clock including daytime napping. In contrast, they may have very little or no napping when their circadian rhythms are aligned with the 24-hour day. In order to measure the effect of this dynamic circadian disorder on daytime napping a robust assessment for measuring the worst of the daytime napping, the 25% worst days will be used for this calculation in a similar fashion as for LQ-nTST.

The method for calculating the UQ-dTSD is described as follows. For a given individual, all non-missing values of daytime total nap durations are summed for a given day and then these daily summations are rank ordered from largest to smallest (Note: days for which an individual reported no nap are recorded as zero). The first 25% (ceiling(number of non-missing records)/4) of the records are flagged as belonging to the upper quartile of daytime total sleep duration (dTSD). The average of these values is calculated and this result is denoted UQ-dTSD.

For example, assume that a subject has 26 dTSD baseline records: 1.083, 1.083, 1.083, 1.083, 1.083, 1.083, 1.083, 1.083, 1.083, 1.083, 1.083, 1.083, 1.083, 1.083, 1.083, 1.083, 1.083, 0, 1.083, 1.667, 1.083, 1.083, 1.083, 1.083, 1.083, and 1.083.

These are rank ordered (largest to smallest) and the first 25% of records, i.e., ceiling(26/4) =7 records identified: 1.667, 1.083, 1.083, 1.083, 1.083, 1.083, and 1.083.

These values are averaged to obtain the subject's UQ-dTSD: (1.667 +1.083 +1.083 +1.083 +1.083+1.083 +1.083)/ 7=1.17.

Midpoint of Sleep Timing (MoST)

Circadian rhythm disorders, including Non-24, are characterized by a timing misalignment of the circadian rhythms to the 24-hour light-dark cycle and hence the activities that an individual is performing (e.g., attempting to sleep at night when the circadian rhythms are signaling the brain to be awake). Midpoint of sleep timing is derived from a combination of the sleep reported in both the pre-and post-sleep questionnaires. The midpoint of sleep timing over a 24 hour period (adjusted to be relative from −12 hours before bedtime until +12 hours after bedtime) can be calculated for each day. The first step in calculating the midpoint is to calculate the midpoint and weight, e.g., duration, for each sleep episode. The total 24-hour sleep time is the summation of all sleep episodes in this 24 hour period. Each of the individual sleep episodes is then assigned a weight relative to the fraction of 24 hour sleep that it contains.

A useful MoST algorithm can be summarized as follows:

1. calculate the midpoint and weight, i.e., duration, for each sleep episode in a given 24 hour period;
2. assign a weight to each sleep episode;
3. determine the average of the weighted sleep episodes; and
4. correct the average of the weighted sleep episodes for target bedtime.

More specifically, such useful algorithm may be further defined as follows: the midpoint for each sleep episode in a 24 hour period is calculated as follows:

Sleep Start Time+[(Sleep End Time−Sleep Start Time)/2]−24;

the weight of each sleep episode is equal to the duration of sleep (as perceived or objectively measured);

the weighted value of each sleep episode is calculated as follows:

midpoint*(weight/TST)

where TST is the sum of all sleep durations in the 24 hour period;

the average of the weighted sleep episodes is the sum of the weighted values of all sleep episodes divided by the number of sleep episodes; and the correction for target bedtime is calculated as follows:

24−target bedtime+average of weighted sleep episodes.

For example, assuming an individual with a target bedtime of 10:30 PM went to sleep at 10:30 PM and woke up at 6:30 AM (with a self-reported total sleep time of 5 hours). Assuming, also, that he/she took a nap at 8:05 PM that lasted 2 hours and 5 minutes. The mid-point of sleep timing (MoST) for that day would be 1.959559 (relative to the target bedtime), calculated as follows.

Nighttime Sleep Midpoint:

Sleep Start Time=Target Bedtime=targetBT=10:30 PM=22.5

Sleep End Time=Wake Time=6:30 AM=6.5

Sleep End Time (adjusted for 24 hour periodicity)=24+6.5=30.5

Nighttime Sleep Midpoint=1(30.5−22.5)/2 modulus 24=2.5 (relative to the midnight)

weight=nTST=5 hours=5.0

Nap Midpoint:

Sleep Start Time=NapStart=08:05 PM=20.08333

NapDuration=02 h 05 m=2.083333

Sleep End Time=NapEnd=NapStart+NapDuration=20.08333+2.083333=22.16667 (10:10 PM)

Nap Midpoint=NapStart+(NapEnd−NapStart)/2=20.08333+[(22.16667−20.08333)/2]−24=−2.875 (relative to the midnight)

weight=NapDuration=2.083333

Weighting of Sleep Episodes

TST=sum(all sleep episodes)=sum(5.0, 2.083333)=7.083333

Weighted Nighttime Sleep=mid*(weight/TST)=2.5*(5/7.083333)=1.7647059

Weighted Nap Sleep=mid*(weight/TST)=−2.875*(2.083333/7.083333)=−0.8455882

Average of Weighted Sleep Episodes

Mean of (1.7647059, −0.8455882)=0.4595588

Correction for Target Bedtime

Correction Amount=24−targetBT=24−22.5=1.5

MoST=0.4595588+1.5=1.959559 (relative to the target bedtime).

Under ideal circumstances in which an individual sleeps at their desired time for 7-8 hours and does not have any daytime naps the MoST will be around 3.5-4.0. In the above hypothetical example, this individual had a late afternoon or night nap which pulls the midpoint below this desired range to 1.96. Alternatively, if a patient has more morning naps then this would potentially lead to a bigger number. If the illustration were changed such that the hypothetical patient slept from 10:30 pm to 6:30 am with no naps, then the patient's MoST would be 4.0. This algorithm dynamically takes into account the information from both the nighttime sleep as well as the daytime napping. Additionally, because the weighted sleep episodes are divided by the total number of sleep episodes within a 24 hour period the derived midpoint of sleep timing will be pushed to 0 (and away from the optimal value of 3.5-4.0) as an individual's sleep becomes more fragmented. An improvement in MoST is defined as an increase in the MoST scale.

A useful clinical response scale (CRS or N24CRS) can be formed by combining the results of all of LQ-nTST, UQ-dTSD, MoST and CGI-C. In an illustrative embodiment, each assessment on the scale is scored as a 1 or 0 depending on whether the pre-specified threshold is achieved or not, as defined in the table that follows. The score for each assessment is summed with a range of 0-4. Individuals with a N24CRS score of ≥3 are classified as having responded to treatment.

Non-24 Scale of Clinical Response

| Assessment | Threshold of response |
|---|---|
| LQ-nTST | >30, >40 or >45 minutes increase in average nighttime sleep duration |
| UQ-dTSD | >30, >40, or >45 minutes decrease in average daytime sleep duration |
| MoST | >20, >25 or >30 minutes increase |
| CGI-C | <1 or <2 from baseline | or any combination or permutation thereof. Increases and decreases in duration, and other scores in the N24CRS, may be determined by comparing baseline, which may be an average of two or more assessments, to post-treatment, which may be an average of two or more post-treatment assessments. For example, the CGI-C scoring of <=1 (or <=2) can be a comparison of baseline score, which may be a single data point or an average of two (or more) scores from assessments taken prior to or shortly after initiation of treatment, to single data point or to an average of two (or more) scores from post-treatment assessments.

In an illustrative embodiment, improvement, i.e., response to treatment, is defined as the coincident demonstration of:
1. shift of tau towards 24 hours and
2. a score of >=3 on the above-described N24CRS.

In such embodiment, tau can be measured using any methodology including but not limited to aMT6 in urine, cortisol, melatonin in blood or saliva, etc., substantially as described above.

A score of >=2 can also indicate improvement, i.e., patient response to treatment.

The data required to calculate parameters such as LQ-nTST, UQ-dTSD, and MoST, can be objectively quantified in sleep studies or, more practically, it can be collected by way of patient questionnaires that ask patients to self-assess, e.g., did the patient sleep, what time did he or she go to bed, how long did it take to fall asleep, etc. In certain clinical studies, subjects will be required to call an Interactive Voice Response System (IVRS) twice a day starting the day after all screening assessments are completed and continue through the randomization phase for 2.5 circadian cycles or 6 months whichever is less. Subjects will call the IVRS twice, once in the morning no later than 1 hour after scheduled awakening to report nighttime sleep parameters (PSQ) and again in the evening no later than 15 minutes after the subjects daily dosing time to report the length and duration of any daytime sleep episode(s) (PreSQ). The IVRS will automatically call back any subject that fails to perform the required calls within the allocated timeframe. One of skill in the art can readily transfer this or similar methodologies to the treatment setting.

It will be appreciated, of course, that other methodologies may be used to ascertain improvement following initiation of treatment or that variations in the above-described methodologies can be employed, e.g., by utilizing other tau determination methods and/or by measuring different or additional sleep parameters.

Illustrative efficacy indicators based on the above include, e.g.:
1. Combined sleep/wake response (>=90 minute increase in LQ-nTST plus a 90 minute decrease in UQ-dTSD);
2. Entrainment of cortisol secretion;
3. Entrainment+45 minute increase in LQ-nTST;
4. Entrainment+45 minute decrease in UQ-dTSD;
5. Entrainment+>=30 minutes increase in MoST;
6. Entrainment+a score of much improved or better on the CGI-C scale;
7. Increase in LQ-nTST;
8. Decrease in UQ-dTSD;
9. Improvement in MoST;
10. Improvement in CGI-C;
11. N24CRS=4;
12. Combined sleep/wake response (>=45 minute increase in LQ-nTST plus a 45 minute decrease in UQ-dTSD).

In carrying out these methods of the invention, the average of multiple pre-treatment and post-treatment assessments can be used to smooth out test to test and/or day to day variability. For example, a baseline MoST can be compared to the average of two post-treatment initiation MoSTs; in this case, preferably, the difference between the two post-treatment MoSTs is less than 2 hours. If the difference is greater than about 2 hours, one or more further MoST assessments can be carried out.

If efficacy is shown, i.e., if a patient is determined to have achieved or to be moving in the direction of a normal circadian rhythm (i.e., 24 hours or up to 24.1 hours), then treatment can be continued. If efficacy is not shown, then a physican or other healthcare worker may wish to discontinue treatment or change the dose of the melatonin agonist, or otherwise alter the treatment method.

The above-described response assessment methodologies can also be utilized for diagnostic purposes. So, for example, a MoST of less than about 3.5, or less than about 3.0, or less than about 2.5 can be an indication that the patient is suffering from a free running circadian rhythm. Such diagnostic can employ one or more of the above-described parameters optionally with other diagnostic markers also being assessed. For example, the patient's MoST score in combination with a tau determination could also be or be part of a useful diagnostic for free running circadian rhythm.

Thus, in one method of treatment that comprises an aspect of this invention, a patient who presents himself or herself to a physician or other healthcare professional with symptoms of a sleep disorder, e.g., difficulty sleeping at night, frequent daytime naps, etc., is first diagnosed by assessment of the patient's MoST, with or without other diagnostic assessments. Such patient who has a low, e.g., less than 3.5 MoST is then treated with a melatonin agonist, e.g., tasimelteon.

In Phase III clinical trials, i.e., safety and efficacy studies in humans, (SET Study), tasimelteon was demonstrated to be useful in entraining Non-24 patients to a 24 hour circadian rhythm. Specifically, patients were orally administered 20 mg tasimelteon per day for at least 12 weeks prior to re-estimating tau. Patients were selected for randomization or open label based on baseline tau estimates. Drug was administered at about 1 hour prior to target sleep time, as determined by patients based on a 9 hour nighttime sleep period.

The SET study was an 84 patient randomized, double-masked, placebo-controlled study in patients with Non-24. The primary endpoints for this study were Entrainment of the melatonin (aMT6s) rhythm to the 24-hour clock and Clinical Response as measured by Entrainment plus a score of greater than or equal to 3 on the following N24CRS:

Non-24 Scale of Clinical Response:

| Assessment | Threshold of response |
|---|---|
| LQ-nTST | >=45 minutes increase in average nighttime sleep duration |
| UQ-dTSD | >=45 minutes decrease in average daytime sleep duration |
| MoST | >20, >25 or >30 minutes increase and a standard deviation <=2 hours during double-masked phase |
| CGI-C | <=2.0 from the average of Day 112 and Day 183 compared to baseline |

A second study (RESET Study) was a 20 patient randomized withdrawal study designed to demonstrate the maintenance effect of 20 mg/day tasimelteon in the treatment of blind individuals with Non-24. Patients were treated with tasimelteon for at least twelve weeks during an open-label run-in phase during the SET Study. Patients who responded to tasimelteon treatment during the run-in phase were then randomized to receive either placebo or tasimelteon (20 mg/day) for 2 months.

Results relating to the primary endpoint of the SET Study are summarized in Table 1A.

TABLE 1A

SET Study - Primary Endpoints Results:

|  | Tasimelteon (%) | Placebo (%) | p-value |
|---|---|---|---|
| Entrainment (aMT6s) | 20.0 | 2.6 | 0.0171 |
| Clinical Response (Entrainment[1] + N24CRS >= 3) | 23.7 | 0.0 | 0.0028 |
| Clinical Response2 (Entrainment[1] + N24CRS >= 2) | 28.9 | 0.0 | 0.0006 |
| N24CRS >= 3[2] | 28.9 | 2.9 | 0.0031 |
| N24CRS >= 2[2] | 57.9 | 20.6 | 0.0014 |

NOTES:
[1]Entrainment status from the randomized portion of the SET study and/or the screening portion of the RESET study
[2]Sensitivity Analysis The SET study also assessed a number of secondary endpoints including Entrainment of cortisol rhythm and a broad range of clinical sleep and wake parameters. These parameters included improvement in the total nighttime sleep in the worst 25% of nights (LQ-nTST), decrease in the total daytime sleep duration in the worst 25% of days (UQ-dTSD) and midpoint of sleep timing (MoST) which is derived from a combination of the sleep reported for both nighttime and daytime. CGI-C is a seven-point rating scale of global functioning with lower scores indicating larger improvements.

TABLE 1B

SET Study - Secondary Endpoints Results

|  | Tasimelteon | Placebo | p-value |
|---|---|---|---|
| Entrainment (cortisol) (%) | 17.5 | 2.6 | 0.0313 |
| N24CRS (LS mean minutes) | 1.77 | 0.67 | 0.0004 |
| CGI-C[1] (LS mean minutes) | 2.6 | 3.4 | 0.0093 |
| LQ-nTST and UQ-dTSD >= 90 min[2] (%) | 23.8 | 4.5 | 0.0767 |
| LQ-nTST and UQ-dTSD >= 45 min[3] (%) | 31.6 | 8.8 | 0.0177 |
| LQ-nTST (LS mean minutes) | 57.0 | 16.8 | 0.0055 |
| UQ-dTSD[1] (LS mean minutes) | −46.2 | −18.0 | 0.0050 |
| MoST (LS mean minutes) | 34.8 | 14.4 | 0.0123 |

NOTES:
[1]For CGI-C and UQ-dTSD smaller numbers indicate improvement.
[2]For this endpoint, only subjects with significant sleep and nap problems at baseline were included.
[3]Sensitivity Analysis The percentage of patients entrained was higher among patients on drug for two complete circadian cycles. It was also higher among patients not taking a beta blocker and lower among patients with very long tau, e.g., tau>=24.7. Among patients on drug for at least two circadian cycles, not on beta blockers, and tau<24.7 hours, the percentage of entrained patients was approximately 85%.

The results of the SET study represent the initial data from the tasimelteon Non-24 Phase III development program and demonstrate the multiple benefits of this novel therapy in treating patients suffering from this rare circadian rhythm disorder. In the SET study, tasimelteon was demonstrated to be safe and well tolerated.

The primary endpoint of the RESET Study was the maintenance of effect as measured by entrainment of the melatonin (aMT6s) rhythm. Results relating to the primary endpoint of the RESET Study are summarized in Table 2A.

TABLE 2A

RESET Study - Primary Endpoint Results:

|  | Tasimelteon | Placebo | p-value |
|---|---|---|---|
| Maintenance of entrainment (aMT6s) (%) | 90.0 | 20.0 | 0.0026 |

The RESET study also assessed a number of secondary endpoints including maintenance of entrainment of the cortisol rhythm and a range of sleep and wake parameters including LQ-nTST (total nighttime sleep in the worst 25% of nights), UQ-dTSD (total daytime sleep duration in the worst 25% of days) and MoST (midpoint of sleep timing from both nighttime and daytime sleep). Results relating to the secondary endpoints of the RESET Study are summarized in Table 2B.

TABLE 2B

RESET Study - Secondary Endpoints Results:

|  | Tasimelteon | Placebo | Difference | p-value |
|---|---|---|---|---|
| maintenance of entrainment (cortisol) (%) | 80.0 | 20.0 | 60.0 | 0.0118 |
| LQ-nTST (LS mean minutes)[1] | −6.6 | −73.8 | 67.2 | 0.0233 |
| UQ-dTSD (LS mean minutes)[2] | −9.6 | 49.8 | −59.4 | 0.0266 |
| MoST (LS mean minutes)[1] | 19.8 | −16.2 | 36.0 | 0.0108 |

NOTES:
[1]Higher number indicates improvement
[2]Lower number indicates improvement From the run-in phase of the study, the rate of entrainment among tasimelteon treated patients ranged from 50% to 85% based on individual patient characteristics. In a time to relapse analysis (45 min decrement of weekly average nighttime sleep), placebo treated patients relapsed in higher numbers and at an earlier time than tasimelteon treated patients (P=0.0907).

The RESET study demonstrates the efficacy of chronic treatment with tasimelteon in Non-24 and further supports the results of the SET study, which established the ability of tasimelteon to entrain the master body clock and significantly improve the clinical symptoms of Non-24.

For maintenance of an entrained circadian rhythm, i.e., chronic treatment, the treatment regimens described herein can be continued daily indefinitely. So, for example, tasimelteon can be administered orally, e.g., at a dose of 20 mg/day, e.g., at about ½ to about 1 hour prior to bedtime.

Results of clinical study also show a strong correlation between endogenous melatonin and efficacy of tasimelteon in entraining patients to a 24 hour circadian rhythm. The following table (Table 3A) compares the peak aMT6s levels in the 24 entrained and 23 non-entrained patients.

TABLE 3A

| Peak aMT6s (ng/hr) Entrained Patients | Peak aMT6s (ng/hr) Non-entrained Patients |
|---|---|
| 291.05 | 261.68 |
| 302.40 | 334.34 |
| 350.92 | 409.12 |
| 362.07 | 472.99 |
| 510.60 | 514.14 |
| 786.85 | 552.77 |
| 811.80 | 552.90 |
| 958.89 | 581.95 |
| 1102.76 | 810.43 |
| 1205.45 | 846.55 |
| 1329.08 | 862.91 |
| 1442.48 | 1155.66 |
| 1502.80 | 1284.35 |
| 2106.44 | 1295.37 |
| 2211.81 | 1397.71 |
| 2226.06 | 1444.94 |
| 2287.07 | 1451.43 |
| 2566.27 | 1622.23 |
| 2706.67 | 1637.45 |
| 2801.31 | 1719.94 |
| 2891.17 | 1749.32 |
| 3391.00 | 2329.65 |
| 3867.45 | 2671.17 |
| 5547.22 | |

The average baseline aMT6s excretion rate in urine, as determined using the methodology described above, was 1814.98 ng/hr in subjects who became entrained in response to tasimelteon therapy and 1128.65 ng/hr in subjects who did not become entrained in response to tasimelteon therapy. Eleven of thirteen patients with a baseline aMT6s excretion rate >2000 ng/hr responded to therapy. See, Table 3B.

TABLE 3B

| | Peak aMT6s (ng/hr) | | | | |
|---|---|---|---|---|---|
| | All | <1500 | ≥1500 | <2000 | ≥2000 |
| Total | 47 | 29 | 18 | 34 | 13 |
| Entrained | 24 (51%) | 12 (41%) | 12 (67%) | 13 (38%) | 11 (85%) |
| Non-entrained | 23 (49%) | 17 (59%) | 6 (33%) | 21 (62%) | 2 (15%) |

Data from these studies currently available also indicate that beta blocker therapy is indirectly related to efficacy of tasimelteon, i.e., patients receiving beta blocker therapy were less likely to become entrained than patients who were not.

TABLE 4

| | Status | |
|---|---|---|
| Taking Beta Blocker | Entrained | Non-entrained |
| No | 24 | 19 |
| Yes | 0 | 4 |

In addition, currently available data indicate a correlation between tau as determined by assaying for aMT6s levels in urine substantially as described above and assaying for cortisol in urine substantially as described above, as shown in Table 5.

TABLE 5

| Site # | Subject # | Tau (aMT6s) | CI Low | CI High | Cycle Length (Days) | Tau (Cortisol) | CI Low | CI High | Cycle Length (Days) | P Value |
|---|---|---|---|---|---|---|---|---|---|---|
| 405 | 3001 | 23.92 | 23.71 | 24.13 | N/A | 23.88 | 23.49 | 24.27 | n/a | 0.32 |
| 410 | 3002 | 24.02 | 23.86 | 24.19 | N/A | 23.92 | 23.64 | 24.21 | N/A | 0.37 |
| 409 | 3003 | 23.97 | 23.77 | 24.17 | N/A | 23.94 | 23.75 | 24.12 | N/A | 0.37 |
| 405 | 3002 | 23.98 | 23.86 | 24.1 | N/A | 23.96 | 23.8 | 24.13 | n/a | 0.46 |
| 405 | 3003 | 23.95 | 23.87 | 24.04 | N/A | 23.97 | 23.78 | 24.15 | n/a | 0.51 |
| 424 | 3003 | 23.96 | 23.8 | 24.12 | N/A | 23.99 | 23.92 | 24.05 | N/A | 0.46 |
| 411 | 3001 | 24.02 | 23.77 | 24.26 | 1482 | 24.01 | 23.48 | 24.54 | 2728 | 0.95 |
| 426 | 3002 | 24.01 | 23.87 | 24.15 | 3959 | 24.01 | 23.54 | 24.48 | 3111 | 0.95 |
| 410 | 3001 | 24.02 | 23.99 | 24.05 | N/A | 24.02 | 23.89 | 24.15 | 1176 | 0.57 |
| 412 | 3002 | 23.99 | 23.88 | 24.09 | N/A | 24.05 | 23.09 | 25.02 | 468 | 0.84 |
| 412 | 3003 | 23.98 | 23.88 | 24.08 | N/A | 24.05 | 23.84 | 24.26 | 460 | 0.4 |
| 409 | 3002 | 24.08 | 23.99 | 24.17 | 290 | 24.08 | 23.95 | 24.21 | 287 | 0.11 |
| 424 | 3001 | 23.97 | 23.68 | 24.26 | N/A | 24.17 | 24.02 | 24.32 | 140 | 0.04 |
| 407 | 3003 | 24.33 | 24.21 | 24.44 | 74 | 24.11 | 23.97 | 24.24 | 225 | 0.08 |
| 410 | 3006 | 24.29 | 23.57 | 25.02 | 83 | 24.12 | 23.65 | 24.58 | 205 | 0.39 |
| 407 | 3001 | 24.56 | 24.37 | 24.75 | 43 | 24.13 | 22.89 | 25.37 | 179 | 0.69 |
| 401 | 3002 | 24.31 | 24.22 | 24.4 | 77 | 24.15 | 24.08 | 24.23 | 158 | 0.01 |
| 406 | 3002 | 24.41 | 22.66 | 26.16 | 59 | 24.3 | 24 | 24.6 | 81 | 0.05 |
| 421 | 3001 | 24.86 | 22.57 | 27.14 | 29 | 24.37 | 21.83 | 26.92 | 65 | 0.31 |

TABLE 5-continued

| Site # | Subject # | Tau (aMT6s) | CI Low | CI High | Cycle Length (Days) | Tau (Cortisol) | CI Low | CI High | Cycle Length (Days) | P Value |
|---|---|---|---|---|---|---|---|---|---|---|
| 406 | 3003 | 24.48 | 24.07 | 24.9 | 50 | 24.42 | 24.25 | 24.59 | 58 | 0.01 |
| 410 | 3004 | 24.39 | 24.27 | 24.51 | 62 | 24.43 | 24.4 | 24.47 | 56 | 0.01 |
| 403 | 3001 | 24.76 | 23.42 | 26.1 | 32 | 24.44 | 24.06 | 24.82 | 55 | 0.04 |
| 419 | 3001 | 25.28 | 25.04 | 25.51 | 19 | 24.54 | 24.07 | 25.02 | 45 | 0.04 |
| 409 | 3001 | 24.52 | 24.41 | 24.63 | 47 | 24.58 | 24.47 | 24.68 | 42 | 0.01 |
| 411 | 3003 | 24.5 | 24.13 | 24.87 | 49 | 24.61 | 24.28 | 24.94 | 40 | 0.02 |
| 411 | 3004 | 24.92 | 24.46 | 25.38 | 27 | 24.74 | 24.15 | 25.34 | 33 | 0.03 |
| 403 | 3002 | 24.8 | 24.59 | 25.01 | 31 | 24.77 | 23.94 | 25.6 | 32 | 0.06 |
| 425 | 3003 | 24.77 | 23.67 | 25.88 | 32 | 24.86 | 23.91 | 25.81 | 29 | 0.06 |
| 425 | 3002 | 25.01 | 24.63 | 25.4 | 24 | 25.1 | 24.65 | 25.55 | 22 | 0.01 |

Data from clinical studies also show that CYP1A2 inhibitors and smoking both affect patient exposure to drug.

Fluvoxamine is a strong CYP1A2 inhibitor. $AUC_{0-inf}$ for tasimelteon increased approximately 7-fold, and the $C_{max}$ increased approximately 2-fold upon co-administration of fluvoxamine and tasimelteon, compared to tasimelteon administered alone.

Table 6 below shows the effect of co-administration of tasimelteon and fluvoxamine on tasimelteon's pharmacokinetics. Twenty-four healthy male or female subjects between the ages of 18 and 55 years of age (inclusive) who were non-smokers with a body mass index (BMI) of ≥18 and ≤35 kg/m2 participated in this open-label, single-sequence study conducted at one site. On day 1, subjects were administered 5.667 mg of tasimelteon. On days 2-7, subjects were administered 50 mg of fluvoxamine. On day 8, subjects were co-administered 5.667 mg of tasimelteon and 50 mg of fluvoxamine.

TABLE 6

| Analyte | Day | Cmax (ng/ml) | Tmax (h) | AUC (inf) (h × ng/mL) | t½ (h) | CL/F (mL/min) |
|---|---|---|---|---|---|---|
| Tasimelteon | 1 | 68.0 ± 28.9 | 0.50 | 102 ± 61.5 | 1.20 ± 0.22 | 107 ± 555 |
| Tasimelteon | 8 | 155 ± 51.1 | 0.50 | 701 ± 402 | 2.59 ± 0.71 | 189 ± 155 |
| Geometric Mean Ratio* (%) | | 232.74 | N/A | 653.36 | 211.82 | 15.31 |
| M12 | 1 | 31.0 ± 7.23 | 0.88 | 189 ± 90.8 | 3.03 ± 1.02 | N/A |
| M12 | 8 | 30.8 ± 17.6 | 3.00 | 435 ± 109.3 | 7.03 ± 3.27 | N/A |
| Geometric Mean Ratio (%) | | 92.74 | N/A | 274.81 | 241.02 | N/A |
| M13 | 1 | 87.5 ± 24.4 | 0.50 | 106 ± 32.6 | 1.00 ± 0.30 | N/A |
| M13 | 8 | 63.6 ± 24.6 | 0.50 | 133 ± 32.9 | 3.51 ± 1.18 | |
| Geometric Mean Ratio (%)* | | 69.31 | N/A | 125.05 | 349.81 | N/A |
| M9 | 1 | 67.6 ± 19.1 | 0.50 | 104 ± 30.0 | 1.14 ± 0.29 | N/A |
| M9 | 8 | 47.4 ± 24.2 | 0.75 | 126 ± 29.6 | 3.83 ± 1.34 | N/A |
| Geometric Mean Ratio (%)* | | 64.94 | N/A | 122.56 | 328.02 | N/A |
| M11 | 1 | 15.8 ± 5.40 | 1.00 | 44.5 ± 17.2 | 1.61 ± 0.55 | N/A |
| M11 | 8 | 11.0 ± 3.94 | 1.00 | 55.8 ± 18.3 | 4.14 ± 1.44 | N/A |
| Geometric Mean Ratio (%)* | | 68.71 | N/A | 126.03 | 248.35 | N/A |
| M14 | 1 | 1.20 ± 0.40 | 0.75 | 4.54 ± 2.39 | 2.18 ± 0.97 | N/A |
| M14 | 8 | 3.20 ± 1.49 | 4.00 | 42.6 ± 27.3 | 4.98 ± 1.89 | N/A |
| Geometric Mean Ratio (%)* | | 264.58 | N/A | 944.73 | 243.34 | N/A |

Figure 5:
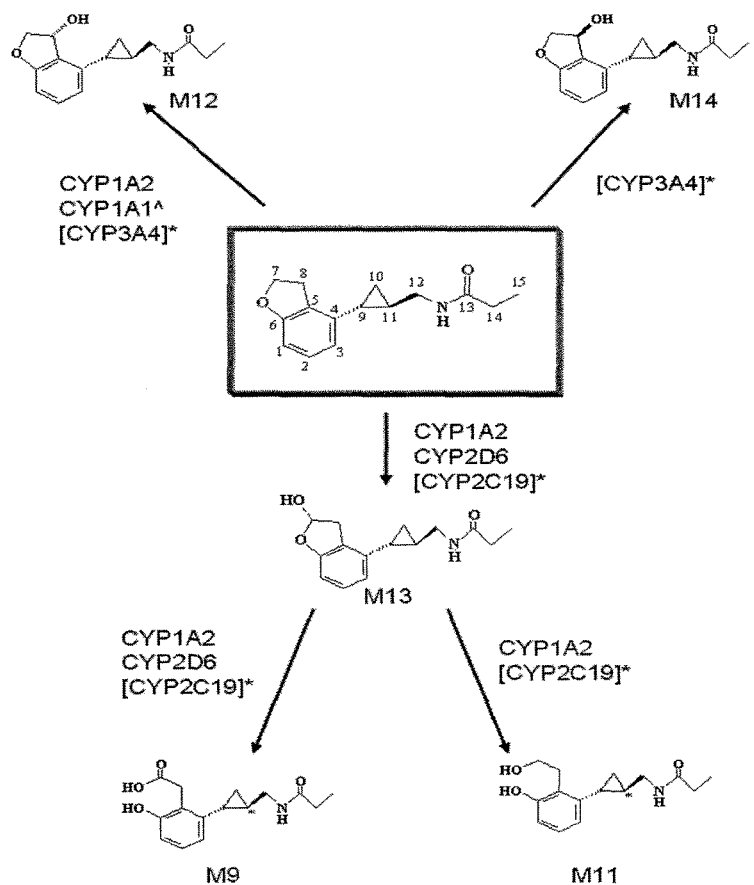
FIG. 5 shows a metabolic pathway of tasimelteon and several of its metabolites.
Figure 6:
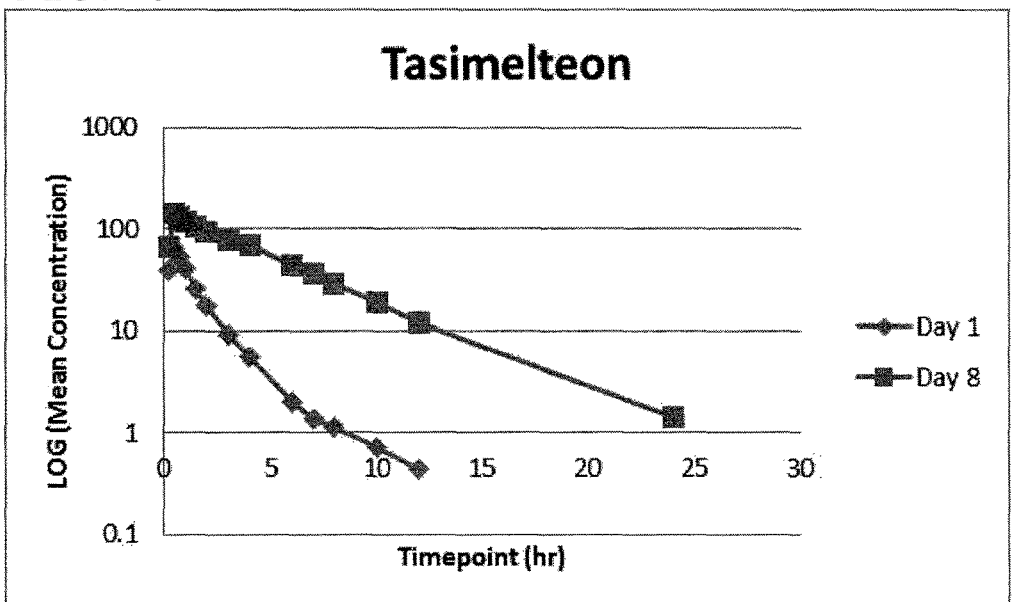
FIGS. 6-11 show plots of the effect of co-administration of tasimelteon and fluvoxamine on the concentration of, respectively, tasimelteon, the M9 metabolite, the M11 metabolite, the M12 metabolite, the M13 metabolite, and the M14 metabolite.
Figure 7:
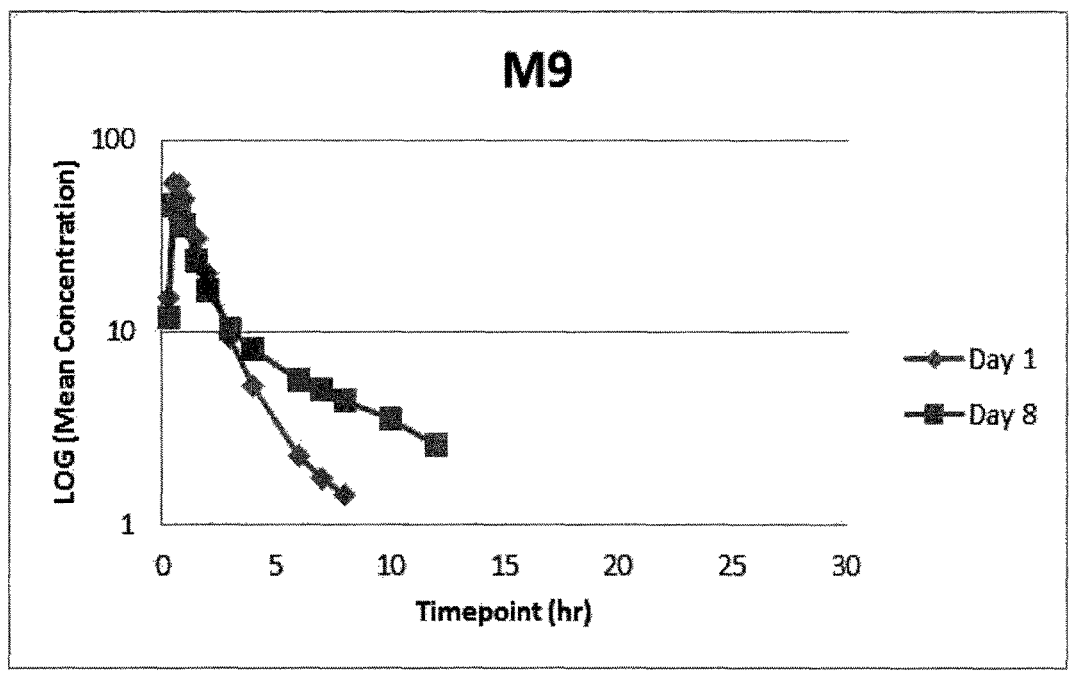
Figure 8:
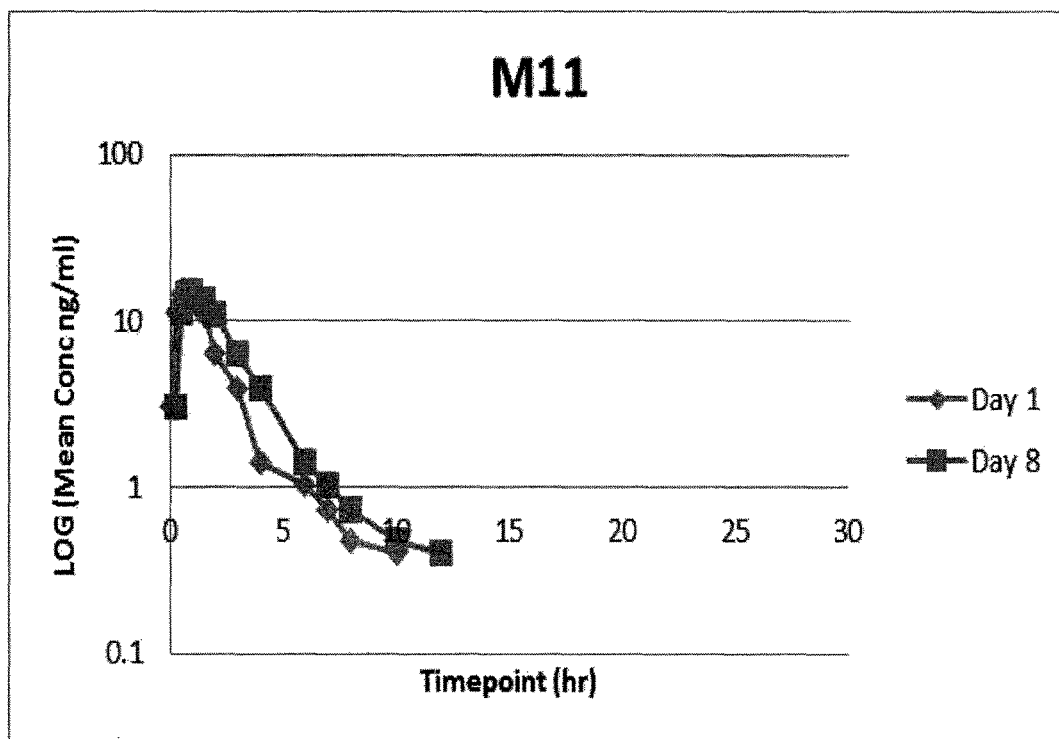
Figure 9:
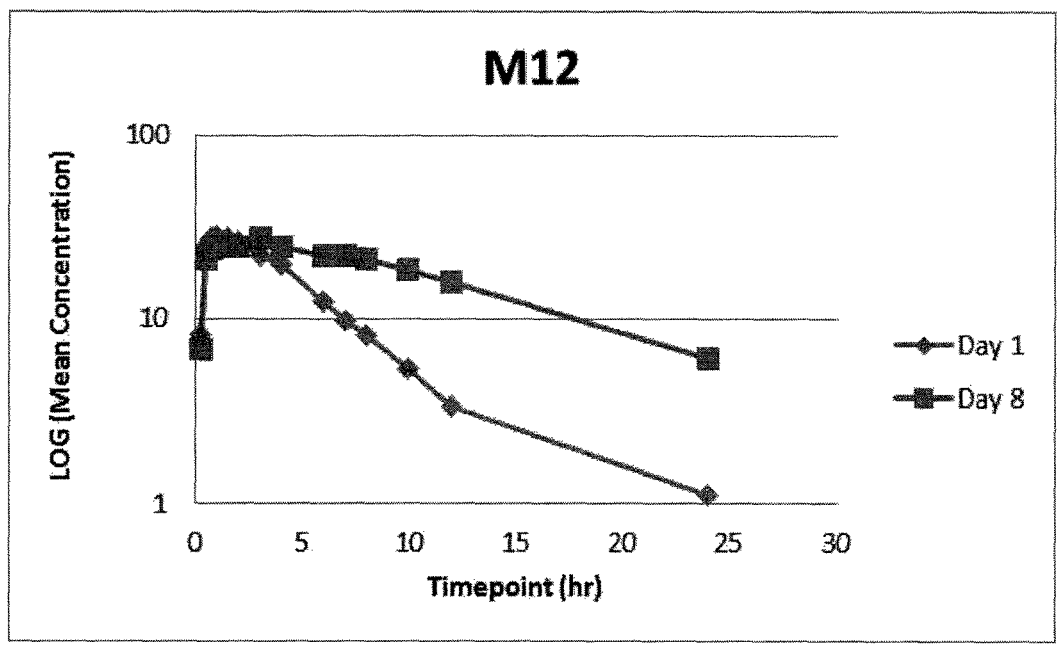
Figure 10:
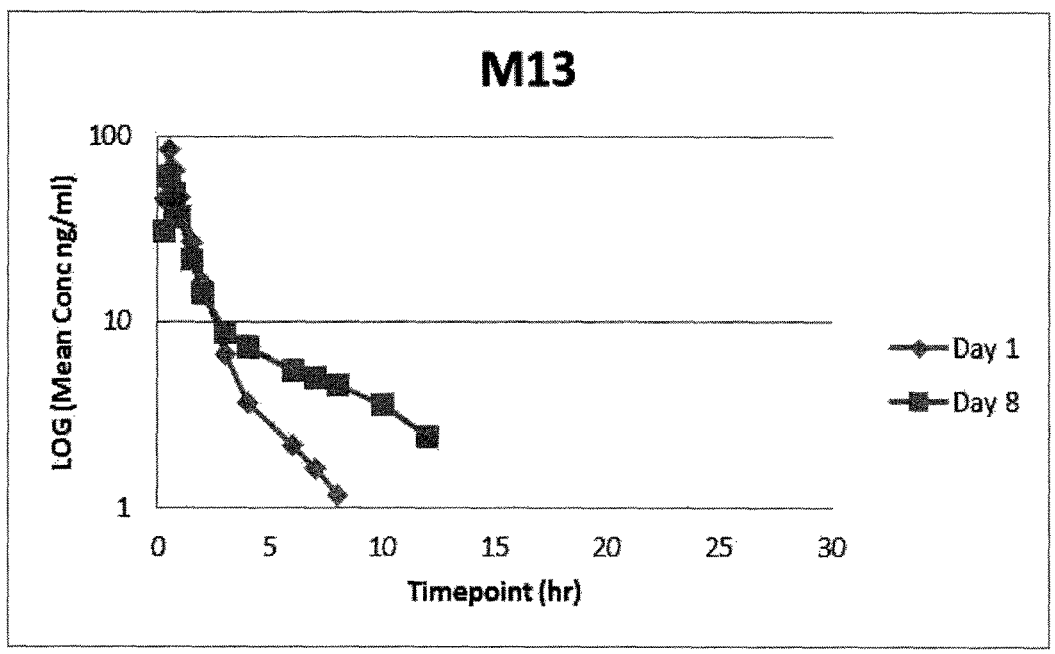
Figure 11:
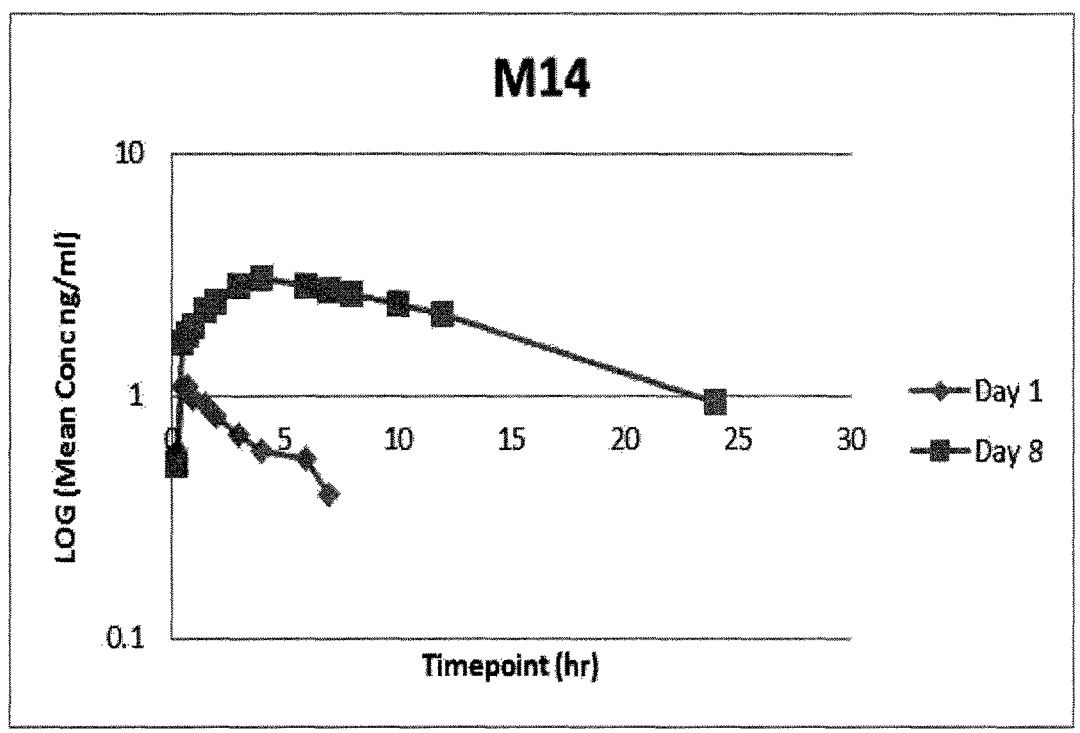
Figure 12:
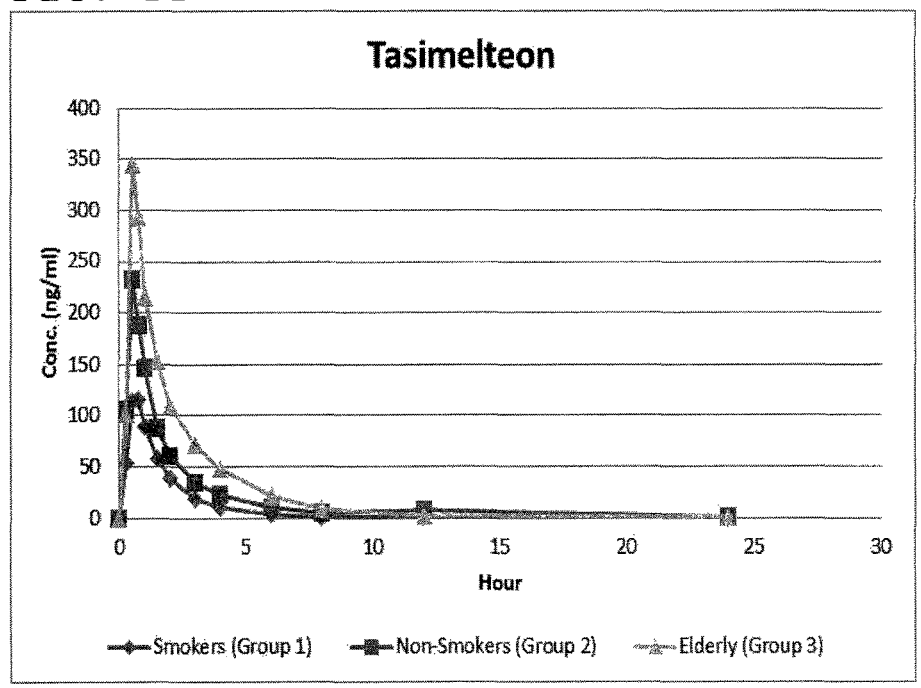
FIGS. 12-17 show plots of the effect of smoking on the concentration of, respectively, tasimelteon, the M9 metabolite, the M11 metabolite, the M12 metabolite, the M13 metabolite, and the M14 metabolite.
Figure 13:
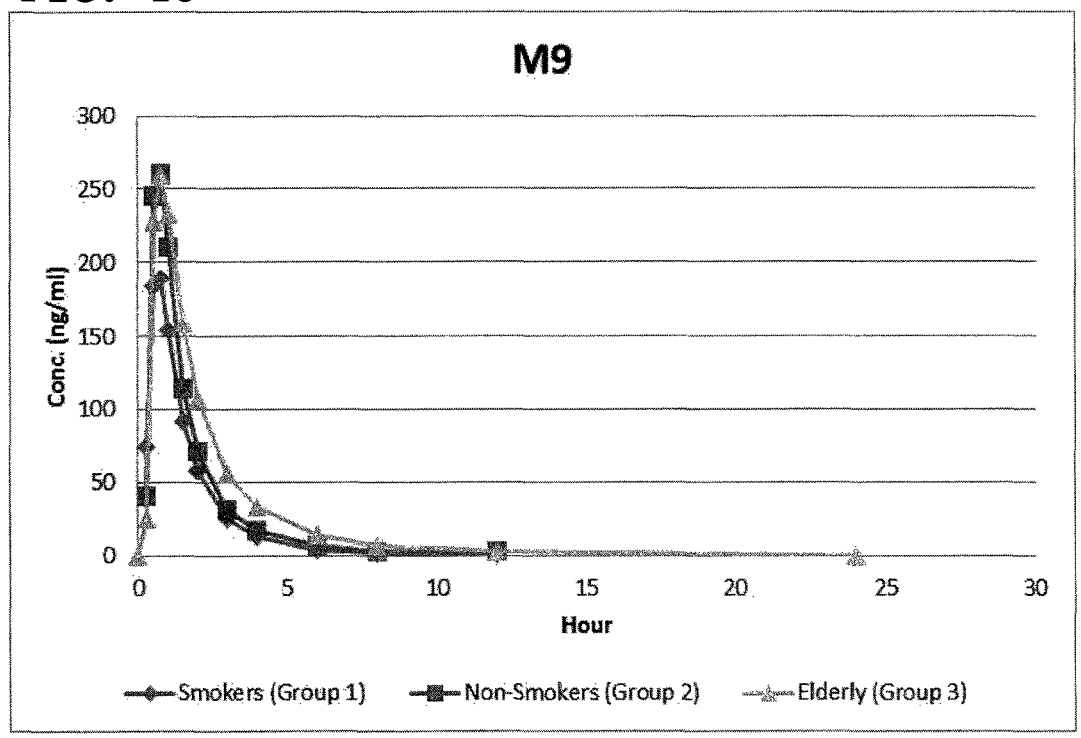
Figure 14:
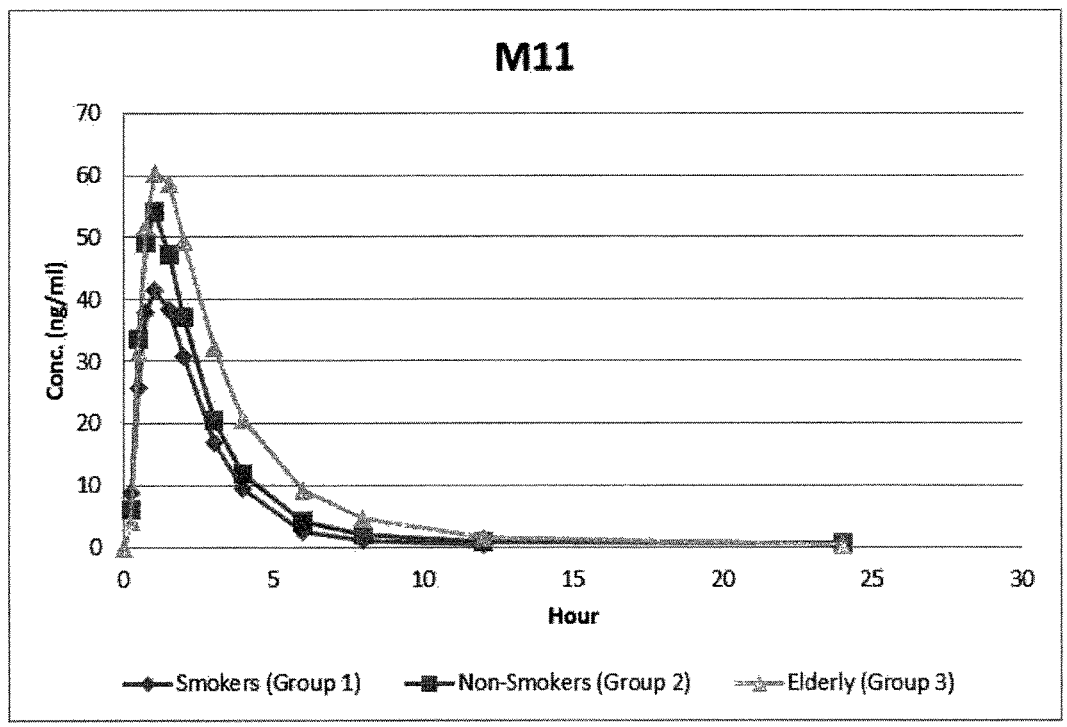
Figure 15:
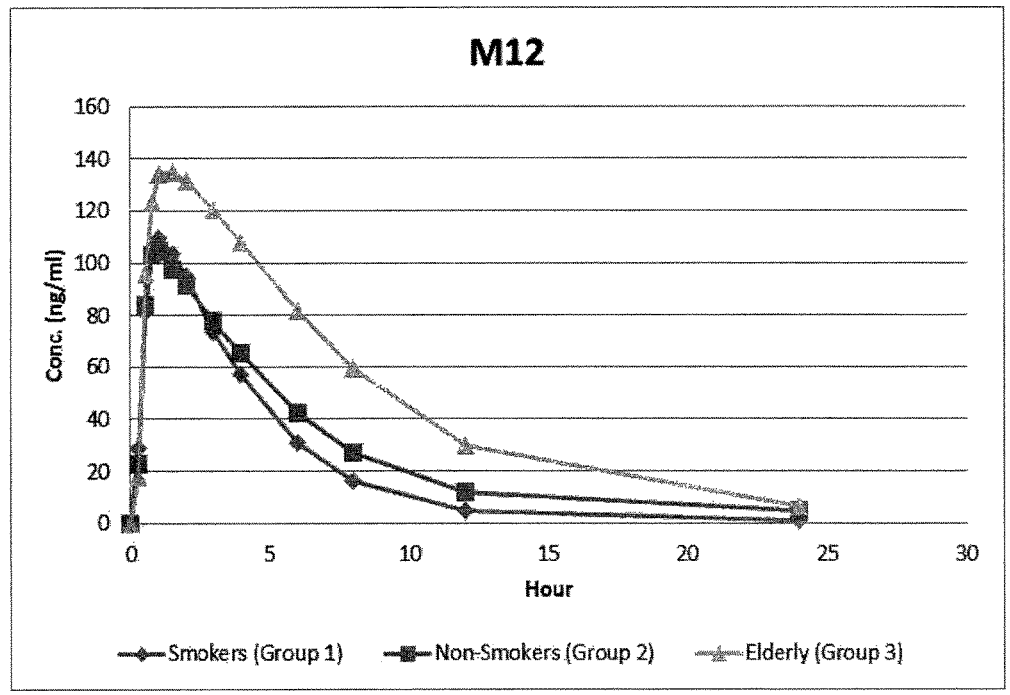
Figure 16:
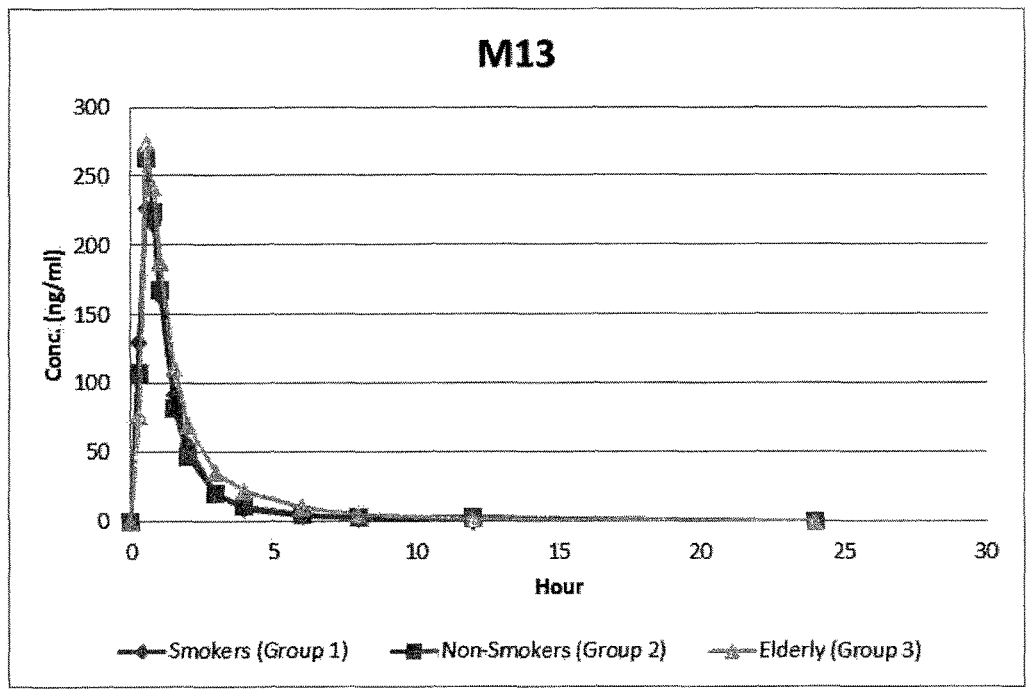
Figure 17:
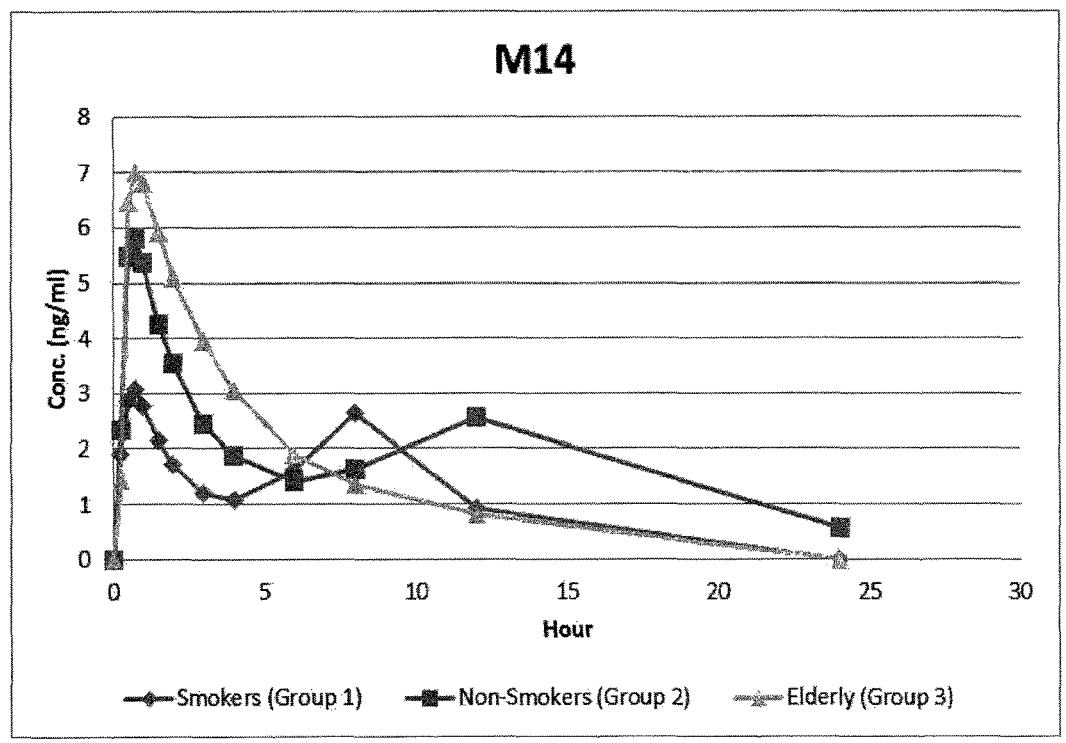

FIG. 5 shows a diagram of a metabolic pathway of tasimelteon. FIGS. 6-11 show plots of the effect of co-administration of tasimelteon and fluvoxamine on the concentration of, respectively, tasimelteon, the M9 metabolite, the M11 metabolite, the M12 metabolite, the M13 metabolite, and the M14 metabolite. As can be seen from FIGS. 6-11, the increase in concentration attributable to fluvoxamine co-administration was more pronounced with respect to tasimelteon and its primary metabolites (M12, M13, M14) than its secondary metabolites (M9, M11).

Table 7 below shows the effect of smoking on the concentration of tasimelteon and several of its metabolites. Smokers were defined as those smoking 10 or more cigarettes per day. Non-smokers were defined as those smoking no cigarettes per day.

TABLE 7

| Analyte | Group | Cmax (ng/ml) | Tmax (h) | AUC (inf) (h × ng/mL) | t½ (h) | CL/F (mL/min) | Vz/F (L) |
|---|---|---|---|---|---|---|---|
| Tasimelteon | Smokers | 136 ± 59.5 | 0.75 | 205 ± 152 | 0.99 ± 0.18 | 2,290 ± 1,232 | 189 ± 94.2 |
| Tasimelteon | Non-Smokers | 239 ± 177 | 0.50 | 389 ± 429 | 1.18 ± 0.46 | 1,482 ± 1,008 | 133 ± 83.0 |
| Geometric Mean Ratio* (%) | | 63.98 | N/A | 60.14 | 86.84 | 166.27 | 144.39 |
| M12 | Smokers | 123 ± 28 | 1.00 | 526 ± 193 | 2.11 ± 0.67 | N/A | N/A |
| M12 | Non-Smokers | 108 ± 29 | 1.00 | 679 ± 433 | 3.05 ± 1.73 | N/A | N/A |
| Geometric Mean Ratio (%) | | 115.53 | N/A | 84.87 | 73.31 | N/A | N/A |
| M13 | Smokers | 272 ± 86 | 0.75 | 329 ± 99 | 0.89 ± 0.26 | N/A | N/A |
| M13 | Non-Smokers | 270 ± 71 | 0.50 | 337 ± 94 | 1.18 ± 0.50 | N/A | N/A |
| Geometric Mean Ratio (%)* | | 99.49 | N/A | 97.31 | 77.51 | N/A | N/A |
| M9 | Smokers | 230 ± 118 | 0.75 | 315 ± 112 | 1.15 ± 0.17 | N/A | N/A |
| M9 | Non-Smokers | 279 ± 82.8 | 0.75 | 406 ± 75 | 1.38 ± 0.45 | N/A | N/A |
| Geometric Mean Ratio (%)* | | 77.18 | N/A | 74.36 | 85.40 | N/A | N/A |
| M11 | Smokers | 46.17 ± 11.9 | 1.00 | 124 ± 42 | 1.99 ± 0.85 | N/A | N/A |
| M11 | Non-Smokers | 54.9 ± 15.1 | 1.00 | 154 ± 58 | 2.14 ± 0.94 | N/A | N/A |
| Geometric Mean Ratio (%)* | | 84.50 | N/A | 81.84 | 94.13 | N/A | N/A |
| M14 | Smokers | 3.72 ± 1.86 | 0.75 | 9.45 ± 11.88 | 1.13 ± 0.54 | N/A | N/A |
| M14 | Non-Smokers | 6.18 ± 3.15 | 0.75 | 22.0 ± 24.2 | 1.84 ± 1.22 | N/A | N/A |
| Geometric Mean Ratio (%)* | | 60.17 | N/A | 42.98 | 65.09 | N/A | N/A |
| M3 | Smokers | 177 ± 71.6 | 0.50 | 239 ± 44.4 | 3.48 ± 2.53 | N/A | N/A |
| M3 | Non-Smokers | 135 ± 49.5 | 0.63 | 194 ± 64.6 | 4.00 ± 2.48 | N/A | N/A |
| Geometric Mean Ratio (%)* | | 131.27 | N/A | 129.43 | 89.16 | N/A | N/A |

FIGS. 12-17 show plots of the effect of smoking on the concentration of, respectively, tasimelteon, the M9 metabolite, the M11 metabolite, the M12 metabolite, the M13 metabolite, and the M14 metabolite.

Related aspects of this invention include computer-based systems comprising means for receiving data concerning treatment-related health information, optionally transiently or indefinitely storing such information, and directly or indirectly transmitting such information to such healthcare professional or patient. Such health information can include whether or not a patient is receiving, i.e., being treated with, a CYP1A2 inhibitor, information relating to a patient's endogenous melatonin levels, information relating to a patient's endogenous cortisol levels, information relating to a patient's tau, information relating to whether or not a patient is receiving, i.e., being treated with, a beta blocker, information relating to whether or not the patient is a smoker, etc.

Accordingly, computer implemented systems and methods using the methods described herein are provided.

For example, related to this invention is a method comprising screening patient test samples to determine melatonin levels, collecting the data, and providing the data to a patient, a health care provider or a health care manager for making a conclusion based on review or analysis of the data. In one embodiment the conclusion is provided to a patient, a health care provider or a health care manager includes transmission of the data over a network.

Melatonin level and circadian rhythm information or other patient specific information such as recited above and as described herein, may be stored in a computer readable form. Such information can also include, e.g., one or more of whether or not a patient is being treated with a CYP1A2 inhibitor, information relating to a patient's endogenous melatonin levels, information relating to a patient's endogenous cortisol levels, information relating to a patient's tau, information relating to whether or not a patient is receiving, i.e., being treated with, a beta blocker, information relating to whether or not the patient is a smoker, etc. Such a computer system typically comprises major subsystems such as a central processor, a system memory (typically RAM), an input/output (I/O) controller, an external device such as a display screen via a display adapter, serial ports, a keyboard, a fixed disk drive via a storage interface and optionally, a disk drive operative to receive a floppy disc, a CD or DVD, or any other data storage medium. Many other devices can be connected, such as a closed or open network interface.

The computer system may be linked to a network, comprising a plurality of computing devices linked via a data link, such as a cable, telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of tau analyses as described herein. Thus in an exemplary embodiment, the determination of peak melatonin levels (or surrogate) and of tau results are provided to a computer where a central processor executes a computer program for determining, e.g., optimal initiation of treatment times, the likelihood of response to treatment, etc.

Also related to this invention is use of a computer system, such as that described above, which comprises: (1) a computer including a computer processor; (2) a stored bit pattern encoding the results obtained by the melatonin analyses of the invention, which may be stored in the computer; (3) and, optionally, (4) a program for determining the likelihood of a therapeutic response.

A computer-based system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

Illustrative reports which can be displayed or projected, or printed, are provided in FIGS. 1, 2, 3, and 4.

A networked client/server architecture can be selected as desired, and can be, for example, a classic two or three tier client server model. A relational database management system (RDMS), either as part of an application server component or as a separate component (RDB machine) provides the interface to the database. In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server (s), including processing on a single machine such as a mainframe, a collection of machines, or other suitable configuration are contemplated. In general, the client and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

The present invention also contemplates a computer-readable storage medium (e.g. CD-ROM, memory key, flash memory card, diskette, etc.) having stored thereon a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program that provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained.

The computer-readable storage medium can also be provided in combination with one or more reagents for carrying out response likelihood assessment.

Also related to this invention are methods of generating a report based on the analyses of melatonin levels in a patient suffering from Non-24. In general, such method can comprise the steps of determining information indicative of the levels of endogenous melatonin, in a biological sample; and creating a report summarizing said information, such as by reporting whether or not a patient is being treated with a CYP1A2 inhibitor, with or without additional information. In one illustrative embodiment of the method, said report includes one or more of an indication of whether or not a patient's melatonin levels achieve a Threshold Concentration, an indication of the patient's cortisol levels, an indication of the patient's tau, an indication of whether or not the patient is being treated with a CYP1A2 inhibitor, information relating to whether or not the patient is a smoker, and an indication of whether or not the patient is being treated with an agent that reduces endogenous melatonin such as a beta blocker.

In some embodiments, the report includes a Threshold Concentration and, optionally, the peak melatonin concentration in the patient's biological sample. In some embodiments, the report includes information relating to the co-administration of tasimelteon and a CYP1A2 inhibitor, such as information relating to increased exposure to tasimelteon that may ensue, information related reducing the dose of tasimelteon or of the CYP1A2 inhibitor, information relating to heightened monitoring, etc. In some embodiments, the report includes information relating to the administration of tasimelteon and smoking, such as information related to decreased exposure to tasimelteon that may ensue, information relating to increasing the dose of tasimelteon, information related to monitoring for levels of tasimelteon in the blood, etc.

Such report can further include one or more of: 1) information regarding the testing facility; 2) service provider information; 3) patient data; 4) sample data; 5) an interpretive report, which can include various information including: a) indication; b) test data, and 6) other features.

In some embodiments, the report further includes a recommendation for a treatment modality for said patient. In such aspect, the report may include information to support a treatment recommendation for said patient, e.g., a recommendation for non-treatment with a melatonin agonist or for heightened monitoring. In all aspects, the report may include a classification of a subject into a group, e.g., likely non-responders or likely responders.

In some embodiments, the report is in electronic form e.g., presented on an electronic display (e.g., computer monitor).

In some embodiments, the report is a visual report comprising:
1) a descriptive title
2) a patient identifier
3) the patient's target initiation of sleep time and one or more of:
(i) a graph of rate of production of melatonin or melatonin surrogate versus time for each Collection Session, the graph showing data points and the calculated circadian cycle including acrophase, each graph being annotated with the projected acrophase and Standard Error,
(ii) a graph of acrophase (time of day) vs. Day showing the projected acrophase determined for each Collection Session and the slope determined by linear regression analysis of the projected acrophase times, said graph being annotated with the length of the patient's tau, the Standard Error and the Confidence Interval expressed both as a p value and as a range of hours, and
(iii) an acrophase table showing the projected time of acrophase for 90 days following the end of the last Collection Session, said table differentially highlighting the date and time of the projected acrophase closest to the target acrophase, the optimal day for initiation of treatment and an estimated window for initiation of treatment.

Such illustrative report is provided in FIG. 1 for a subject that is not suffering Non-24 and in FIG. 2 for a patient that is suffering from N24SWD.

A person or entity who prepares a report ("report generator") may also perform the likelihood assessment. The report generator may also perform one or more of sample gathering, sample processing, and data generation, e.g., the report generator may also perform one or more of: a) sample gathering; b) sample processing; c) measuring melatonin or melatonin surrogate levels. Alternatively, an entity other than the report generator can perform one or more sample gathering, sample processing, and data generation.

For clarity, it should be noted that the term "user," which is used interchangeably with "client," is meant to refer to a person or entity to whom a report is transmitted, and may be the same person or entity who does one or more of the following: a) collects a sample; b) processes a sample; c) provides a sample or a processed sample; and d) generates data for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician, etc.).

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice or liability insurance, or policy), results, whether generated wholly or partially electronically, are subjected to a quality control routine prior to release to the user.

In another aspect, the present disclosure concerns methods of preparing a personalized pharmacologic profile for a patient by a) determining the patient's levels of endogenous melatonin or melatonin surrogate; and (b) creating a report summarizing the data and/or compiling such data with other data relevant to understanding the patient's specific pharmacologic characteristics and condition. In accordance with the method of this invention, the dosage of tasimelteon to be administered will depend on various factors such as the characteristics of the subject being treated, e.g., the severity of disorder, responsiveness to melatonin agonists, age, weight, health, types of concurrent treatment, if any, etc.

The above described computer-implemented methods, systems, reports, etc., can also be applied to determination of efficacy of treatment, such as but not limited to the efficacy determination methodologies described above. For example, computer-based systems can be used to record and report information relating to one or more of MoST, LQ-nTST, UQ-dTSD and CGI-C and/or to tau determinations made prior to or shortly after initiation of therapy as well as subsequent tau determinations.

By way of further illustration, related aspects of this invention include computer-based systems comprising means for receiving data concerning one or more of MoST, LQ-nTST, UQ-dTSD and CGI-C and/or to tau determinations made prior to or shortly after initiation of therapy as well as subsequent tau determinations;

a method comprising collecting data relating to one or more of MoST, LQ-nTST, UQ-dTSD and CGI-C and/or to tau determinations made prior to or shortly after initiation of therapy as well as subsequent tau determinations and providing the data to a patient, a health care provider or a health care manager for making a conclusion based on review or analysis of the data. In one embodiment the conclusion is provided to a patient, a health care provider or a health care manager includes transmission of the data over a network;

information relating to one or more of MoST, LQ-nTST, UQ-dTSD and CGI-C and/or to tau determinations made prior to or shortly after initiation of therapy as well as subsequent tau determinations stored in a computer readable form; a computer system as described above for receiving, storing and outputting such information, optionally linked to a network and optionally comprising code for interpreting the results of efficacy assessment(s) as described herein;

a computer-readable storage medium (e.g., CD-ROM, memory key, flash memory card, diskette, etc.) having stored thereon a program which, when executed in a computing environment, provides for implementation of algorithms to carry out all or a portion of the analysis of efficacy assessments as described herein;

methods of generating a report based on the efficacy assessments as described herein, e.g., a report that includes one or more of an indication of whether or not a patient is responding to therapy.

Such information, databases, systems, methods, analyses, reports, profiles, outputs, recommendations, etc., can be incorporated into storage media, computer systems, and networks, such as are described hereinabove with respect to other parameters, e.g., melatonin levels, circadian rhythms, cortisol levels, tau, co-treatment with CYP1A2 inhibitors, co-treatment with a beta blocker, and smoking, with or without information relating to some or all of such other parameters.

An effective dose is one that over a period of time of treatment, which may be, e.g., 1 day or multiple weeks, results in entrainment of the patient to a 24 hour circadian rhythm. Patients whose tau is reduced to 24 hours, e.g., <24.1 hrs, with a 95% confidence interval that includes 24.0 can be considered to have been entrained, although other values can also be used to define successful entrainment.

The daily dose of tasimelteon useful in entraining patients with Non-24 to a 24 hour circadian rhythm will, in general, be in the range of about 1 to about 100 mg, e.g., about 10 to about 100 or about 20 to about 50. A dose of 20 mg is typically sufficient, in particular, for individuals who are not also being administered a CYP1A2 inhibitor or a beta blocker or who are not smokers.

Similar doses may be employed when entraining a patient's cortisol circadian rhythm.

As discussed above, it has been found that co-administration of tasimelteon with CYP1A2 inhibitors unexpectedly increases the concentration of tasimelteon. This is likely a consequence of inhibition of CYP1A2-mediated conversion of tasimelteon to a metabolite.

CYP1A2 inhibitors include, for example, fluoroquinolone antibiotics, such as ciprofloxacin, SSRIs such as fluvoxamine, and calcium channel blockers such as verapamil. Accordingly, in the case that a patient is to be administered a dose of tasimelteon as part of an attempt to entrain the patient to a 24-hour circadian rhythm and that patient is also being treated with a CYP1A2 inhibitor, it may be necessary or desirable to reduce the dose of tasimelteon, the dose of the CYP1A2 inhibitor, or both. Alternatively, or in addition, it may be necessary or desirable to monitor the patient's plasma concentration of tasimelteon or monitor the patient for an adverse reaction associated with tasimelteon.

For example, the dose of tasimelteon administered to a patient also being treated with a CYP1A2 inhibitor may be reduced to less than 20 mg per day, e.g., about 15 to about 19 mg per day, about 10 to about mg per day, or about 5 to about 10 mg per day, e.g., 5, 6, 7, 8, 9, 10, 11, 12, 13, 14, 15, 16, 17, 18, or 19 mg/day. In some cases, the dose of tasimelteon or the dose of the CYP1A2 inhibitor may be reduced to zero. In an embodiment of the invention, tasimelteon is not be used in combination with fluvoxamine. Other less strong CYP1A2 inhibitors have not been adequately studied. Tasimelteon should be administered with caution to patients taking less strong CYP1A2 inhibitors.

Aspects of the invention, as they relate to the effects of a CYP1A2 inhibitor on tasimelteon exposure, include, without limitation, the following:

treating a patient with tasimelteon wherein the patient is also being treated with a CYP1A2 inhibitor, said method comprising one or more of the following: reducing the dose of tasimelteon, reducing the dose of the CYP1A2 inhibitor, monitoring the patient's plasma concentration of tasimelteon, or monitoring the patient for an adverse reaction associated with tasimelteon;

treating a patient with tasimelteon wherein the patient is also being treated with a substance that is a known inhibitor of CYP1A2, said method comprising monitoring the patient for a potential or actual adverse event associated with increased plasma concentration of tasimelteon while the patient is being coadministered tasimelteon and the CYP1A2 inhibitor;

treating a patient suffering from a sleep disorder wherein such patient is being treated with a CYP1A2 inhibitor, the method comprising: internally administering tasimelteon to the patient in a reduced amount relative to an amount that would be administered to a patient suffering from a sleep disorder but not being treated with a CYP1A2 inhibitor;

a computing device having a processor; a storage device containing information that the patient is being treated with a CYP1A2 inhibitor; an input device for inputting to either or both of the computing device or the storage device information that the patient will be prescribed a dose of tasimelteon; a computer program operable retrieve from the storage device the information that the patient is being treated with a CYP1A2 inhibitor upon inputting the information that the patient will be prescribed the dose of tasimelteon; and an output device for outputting to a user the information that the patient is being treated with a CYP1A2 inhibitor;

a computer-implemented method of treating a patient suffering from a sleep disorder, the method comprising: entering into an electronic database information related to the treatment of a patient with tasimelteon; searching, using a computing device, a medical record of the patient for information related to the current treatment of the patient with an agent other than tasimelteon; and determining, using the computing device, whether the agent other than tasimelteon is a CYP1A2 inhibitor;

a pharmaceutical composition for the treatment of a sleep disorder in an individual being treated with a CYP1A2 inhibitor, the composition comprising: a pharmaceutically-acceptable carrier; and a quantity of tasimelteon corresponding to a daily dosage of less than 20 mg.

In another embodiment, patients who are receiving a CYP1A2 inhibitor, e.g., fluvoxamine, are not treated with tasimelteon. In a related embodiment, patients are instructed not to receive, and healthcare providers are instructed not to prescribe, tasimelteon if the patient is already receiving a CYP1A2 inhibitor, e.g., fluvoxamine.

Smoking, on the other hand, has been found to increase the clearance of tasimelteon, thereby reducing patient exposure. Accordingly, administration of tasimelteon or a tasimelteon metabolite to an individual who smokes may, in some cases, require increasing the dose of tasimelteon or tasimelteon metabolite and/or reducing or eliminating the individual's smoking.

Accordingly, in the case that a patient is to be administered a dose of tasimelteon as part of an attempt to entrain the patient to a 24-hour circadian rhythm and that patient is also a smoker, it may be necessary or desirable to increase the dose of tasimelteon. Alternatively, or in addition, it may be necessary or desirable to monitor the patient's plasma concentration of tasimelteon.

For example, the dose of tasimelteon administered to a patient who also smokes may be increased to greater than 20 mg per day, e.g., 25 mg per day, 30 mg per day, 40 mg per day, 50 mg per day or even 100 mg per day.

Aspects of the invention, as they relate to the effects of smoking on tasimelteon exposure, include, without limitation, the following:

treating a patient with tasimelteon wherein the patient is a smoker, said method comprising one or more of the following: increasing a dose of tasimelteon, monitoring the patient's blood levels of tasimelteon, and instructing the patient to reduce or eliminate smoking;

treating a patient suffering from a sleep disorder wherein such patient is a smoker, the method comprising: internally administering tasimelteon to the patient in an increased amount relative to an amount that would be administered to a patient suffering from a sleep disorder who is not a smoker;

a system comprising: at least one computing device having a processor; a storage device containing information that the patient is a smoker; an input device for inputting to either or both of the computing device or the storage device information that the patient will be prescribed a dose of tasimelteon; a computer program operable retrieve from the storage device the information that the patient is a smoker upon inputting the information that the patient will be prescribed the dose of tasimelteon; and an output device for outputting to a user the information that the patient is a smoker;

a computer-implemented method of treating a patient suffering from a sleep disorder, the method comprising: entering into an electronic database information related to the treatment of a patient with tasimelteon; searching, using a computing device, a medical record of the patient for information related to whether the patient is a smoker; and determining, using the computing device, whether the patient is a smoker;

a pharmaceutical composition for the treatment of a sleep disorder in an individual who smokes, the composition comprising: a pharmaceutically-acceptable carrier; and a quantity of tasimelteon corresponding to a daily dosage of greater than 20 mg.

In general, the melatonin (MT1 and MT2 receptors) agonist, e.g., tasimelteon, is administered in a pharmaceutical formulation q.d. prior to the start of the target sleep time. It has been found that in treating Non-24, it is not necessary to administer the drug more than about 1 hour prior to the start of the target sleep time such that the drug can be administered, e.g., at about 0.5 to about 1.5 hours prior to sleep time. Administration about 1 hour prior to sleep time is convenient and useful. However, this invention also contemplates administration at earlier times in the day, e.g., about 2 hours, or about 3 hours or even about 4 hours prior to target sleep time.

The ability to administer tasimelteon as little as about one hour prior to sleep time is advantageous because it allows for avoidance of pre-sleep time soporific effects, because it allows for administration of higher doses that might have greater soporific effects, and because it allows for pharmacologic intervention at a different phase of the sleep cycle than if it were administered earlier. Without wishing to be bound to any particular theory, it appears that the ability to administer tasimelteon so close to sleep time is a function of its $t_{max}$, which is approximately one-half hour. Melatonin, on the other hand, which has a $t_{max}$ of approximately 2 hours or more, is administered several hours before sleep time, which can cause premature sleepiness; to avoid this soporific effect, melatonin is sometimes administered at sub-optimal doses.

Thus, in a related aspect, this invention comprises a method of treating Non-24 patients, i.e., entraining such patients to a 24 hour circadian rhythm by internally administering an effective amount of a tasimelteon or another melatonin agonist that has a $t_{max}$ of less than about 2 hours, e.g., less than about 1.5 hours, or even less than about 1 hour such as about one-half hour like tasimelteon. Pharmaceutical compositions can be formulated so as to alter $t_{max}$. Thus, e.g., use of an active pharmaceutical ingredient such as melatonin that is formulated such that its $t_{max}$ is less than about two hours, e.g., less than about 1.5 hours, or even less than about 1 hour, to treat Non-24 is an aspect of this invention.

Pharmaceutical compositions to be used comprise a therapeutically effective amount of tasimelteon or an active metabolite of tasimelteon, or a pharmaceutically acceptable salt or other form (e.g., a solvate) thereof, together with one or more pharmaceutically acceptable excipients. The phrase "pharmaceutical composition" refers to a composition suitable for administration in medical use. It should be appreciated that the determinations of proper dosage forms, dosage amounts, and routes of administration for a particular patient are within the level of ordinary skill in the pharmaceutical and medical arts.

Administration is typically oral but other routes of administration are useful, e.g., parenteral, nasal, buccal, transdermal, sublingual, intramuscular, intravenous, rectal, vaginal, etc. Solid dosage forms for oral administration include capsules, tablets, pills, powders, and granules. In such solid dosage forms, the compound is admixed with at least one inert pharmaceutically acceptable excipient such as (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, dragees, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Solid compositions for oral administration can be formulated in a unit dosage form, each dosage containing from about 1 to about 100 mg of active ingredient. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the required pharmaceutical carrier. Tasimelteon can be formulated, e.g., in a unit dosage form that is a capsule having 20 mg of active in addition to excipients.

Liquid dosage forms for oral administration include pharmaceutically acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

The present invention can be carried out in conjunction with other treatment approaches, e.g., in combination with a second or multiple other active pharmaceutical agents, including but not limited to other agents that affect insomnia, sleep-wake patterns, vigilance, depression, or psychotic episodes.

While this invention has been described in conjunction with the specific embodiments outlined above, it is evident that many alternatives, modifications and variations will be apparent to those skilled in the art or are otherwise intended to be embraced. Accordingly, the embodiments of the invention as set forth above are intended to be illustrative, not limiting. Various changes may be made without departing from the spirit and scope of the invention as defined in the following claims. All patents, patent application, scientific articles and other published documents cited herein are hereby incorporated in their entirety for the substance of their disclosures.

What is claimed is:

1. A method of treating a disorder associated with a desynchronous cortisol circadian rhythm in an individual having a desynchronous cortisol circadian rhythm, said method comprising internally administering to the individual an effective amount of tasimelteon,
   wherein the disorder associated with a desynchronous cortisol circadian rhythm is selected from a group consisting of: obesity, depression, and neurological impairment.

2. The method of claim 1, wherein the individual is light perception impaired (LPI).

3. The method of claim 1, wherein the individual is totally blind.

4. The method of claim 1, wherein the individual suffers from Non-24-Hour Sleep-Wake Disorder.

5. The method of claim 1, wherein the effective amount is an amount sufficient to entrain the individual's cortisol circadian rhythm to a natural day/night cycle comprising a 24-hour sleep-wake cycle in which the individual awakens at or near a target wake time following a daily sleep period of approximately seven to nine hours.

6. The method of claim 1, wherein the tasimelteon or active metabolite thereof is administered 0.5 hour to 1.5 hours before a target bedtime.

7. The method of claim 1, wherein the administering includes administering between about 10 mg and about 100 mg of tasimelteon.

8. The method of claim 1, wherein the administering includes administering between about 20 mg and about 50 mg of tasimelteon.

9. The method of claim 1, wherein the administering includes administering about 20 mg of tasimelteon.

* * * * *